US012653464B2

(12) United States Patent
Lee et al.

(10) Patent No.: US 12,653,464 B2
(45) Date of Patent: Jun. 16, 2026

(54) AUTONOMOUS HEALTHCARE VISUAL SYSTEM FOR REAL-TIME PREVENTION, DIAGNOSTICS, TREATMENTS AND REHABILITATION

(71) Applicant: Planned Systems International, Inc., Arlington, VA (US)

(72) Inventors: June Lee, North Bethesda, MD (US); Thomas J. Berti, Lusby, MD (US); Yan Li, Bethesda, MD (US)

(73) Assignees: Planned Systems International, Inc., Arlington, VA (US); National Society of Medical Scientists, Bethesda, MD (US)

( * ) Notice: Subject to any disclaimer, the term of this patent is extended or adjusted under 35 U.S.C. 154(b) by 101 days.

(21) Appl. No.: 18/516,177

(22) Filed: Nov. 21, 2023

(65) Prior Publication Data
US 2024/0090846 A1 Mar. 21, 2024

Related U.S. Application Data

(63) Continuation-in-part of application No. 17/870,621, filed on Jul. 21, 2022, which is a continuation-in-part
(Continued)

(51) Int. Cl.
A61B 5/00 (2006.01)
G06T 7/00 (2017.01)
(Continued)

(52) U.S. Cl.
CPC .......... *A61B 5/7267* (2013.01); *A61B 5/0077* (2013.01); *A61B 5/7246* (2013.01);
(Continued)

(58) Field of Classification Search
CPC ... A61B 5/7267; A61B 5/0077; A61B 5/7246; A61B 2562/0233; A61B 5/0073;
(Continued)

(56) References Cited

U.S. PATENT DOCUMENTS

2011/0130636 A1 6/2011 Daniel et al.
2016/0244163 A1 8/2016 Peeters et al.
(Continued)

OTHER PUBLICATIONS

Yip et al., "Robot Autonomy for Surgery", World Scientific Review, arXiv preprint arXiv:1707.03080, 2017, 33 pages.
(Continued)

*Primary Examiner* — Bo Joseph Peng

(57) ABSTRACT

Systems, methods, and other embodiments relate to autonomous clinical screening and assessment of a patient using a reinforcement learning framework. In at least one approach, a method includes determining, using a control model, a focus point for acquiring imaging data about the patient. The method includes controlling an imaging device according to the focus point to acquire the imaging data. The method includes analyzing the imaging data using a recognition model that outputs a result about a condition of the patient. The method includes providing the result.

20 Claims, 10 Drawing Sheets

Related U.S. Application Data of application No. 17/836,264, filed on Jun. 9, 2022, now Pat. No. 12,283,378.

(60) Provisional application No. 63/390,816, filed on Jul. 20, 2022.

(51) Int. Cl.

| | |
|---|---|
| *G06T 7/70* | (2017.01) |
| *G16H 40/63* | (2018.01) |
| *G16H 50/20* | (2018.01) |
| *H04N 23/67* | (2023.01) |
| *H04N 23/69* | (2023.01) |

(52) U.S. Cl.

CPC ............. *G06T 7/0012* (2013.01); *G06T 7/70* (2017.01); *G16H 40/63* (2018.01); *G16H 50/20* (2018.01); *H04N 23/67* (2023.01); *H04N 23/69* (2023.01); *A61B 2562/0233* (2013.01); *G06T 2207/20081* (2013.01); *G06T 2207/20084* (2013.01); *G06T 2207/30032* (2013.01); *G06T 2207/30096* (2013.01)

(58) Field of Classification Search

CPC . A61B 5/14532; A61B 5/0035; A61B 5/0066; A61B 5/0071; A61B 5/021; A61B 5/024; A61B 5/055; A61B 5/1114; A61B 5/318; A61B 5/4887; A61B 5/725; A61B 5/7285; G06T 7/0012; G06T 7/70; G06T 2207/20081; G06T 2207/20084; G06T 2207/30032; G06T 2207/30096; G06T 7/80; G16H 40/63; G16H 50/20; G16H 30/20; G16H 30/40; G16H 50/30; G16H 50/70; H04N 23/67; H04N 23/69; G06V 10/147; G06V 10/82; G06V 20/693; G06V 20/69; G06V 2201/03

See application file for complete search history.

(56) References Cited

U.S. PATENT DOCUMENTS

| | | | |
|---|---|---|---|
| 2017/0092109 A1 | 3/2017 | Trundle et al. | |
| 2017/0329916 A1* | 11/2017 | Bychkov | G16H 10/60 |
| 2018/0322660 A1* | 11/2018 | Smith | G06T 7/97 |
| 2019/0008598 A1 | 1/2019 | Frimer et al. | |
| 2019/0117181 A1* | 4/2019 | Ishii | A61B 6/487 |
| 2019/0262084 A1 | 8/2019 | Roh et al. | |
| 2020/0027560 A1 | 1/2020 | Ling et al. | |
| 2020/0035335 A1 | 1/2020 | Kivatinos et al. | |
| 2020/0098461 A1 | 3/2020 | Macoviak et al. | |
| 2020/0111578 A1 | 4/2020 | Koblick et al. | |
| 2020/0302144 A1* | 9/2020 | Leshem | G06V 20/647 |
| 2020/0338309 A1 | 10/2020 | Kopperschmidt et al. | |
| 2021/0327578 A1 | 10/2021 | Buchard et al. | |
| 2022/0037039 A1 | 2/2022 | Wein | |
| 2022/0047339 A1 | 2/2022 | Prior et al. | |

OTHER PUBLICATIONS

Sahashi, et al.,"A study of operational liability of the medical rescue robot under disaster," 2011 IEEE/SICE International Symposium on System Integration (SII), 2011, 6 pages.

* cited by examiner

SCREENING          MAPPING          DETECTION

AL- 2

AL- n 120
115
110
AL- 1
105

10m
1m
10cm
1cm
10mm
1mm
100um
10um
1um
100nm
10nm
1nm

FOCAL
POINT 1
FOCAL
POINT 2
FOCAL
POINT J

125

Sphere Lens Arrays     Active Learning     Learn Via Deep Reinforcement

Deep Reinforcement Learning-Based Imaging Device

100

200

**AUTONOMOUS
MULTIFOCAL LENS
ARRAYS**

LENS BODY 501

BEAM ARC 502

INNER CONTOUR 503

TRANS DELAY LINES 504

ROBOT ARRAYS 505

ROBOT CHIPS 506

ROBOT MARKERS 507

CONTROLLER

L1     L2     L3

BEAM
PORTS

ARRAY PORTS

500

LENS BODY

BEAM ARC

INNER CONTOUR

TRANS DELAY LINES

ROBOT ARRAYS

ROBOT CHIPS

ROBOT MARKERS

Field 1

Field 2

Field J

Field ALL

Field 3

Field 4

Field n $X_1, Y_1$ $X_j, Y_j$ $X_2, Y_2$

600

900                    901                    902

903

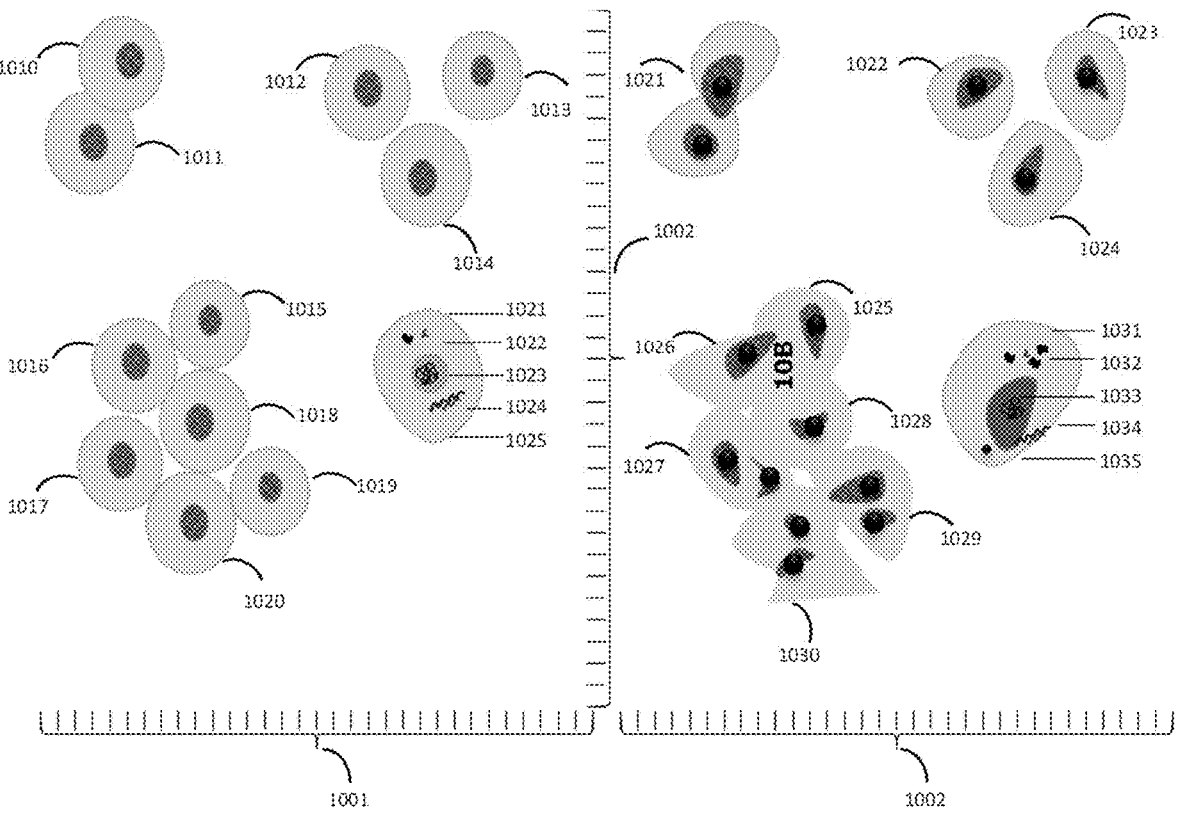
FIG. 10A                    FIG. 10B

AUTONOMOUS HEALTHCARE VISUAL SYSTEM FOR REAL-TIME PREVENTION, DIAGNOSTICS, TREATMENTS AND REHABILITATION

CROSS-REFERENCE TO RELATED APPLICATIONS

This application is a continuation in part of and claims the benefit of U.S. Non-Provisional application Ser. No. 17/870,621, filed on Jul. 21, 2022, which claims priority to U.S. Provisional Application No. 63/390,816 filed on Jul. 20, 2022 and is a continuation in part of and claims the benefit of U.S. Non-Provisional application Ser. No. 17/836,264, filed on Jun. 9, 2022, which are all herein incorporated by reference in their entirety.

TECHNICAL FIELD

The present disclosure relates, in one aspect, to autonomous clinical screening/assessment and, in particular, to the autonomous control of an imaging device using reinforcement learning.

BACKGROUND

Health Professionals perform clinical screening and assessment as a primary task. To execute these tasks, the health professionals use their knowledge, experience, and clinical judgment to assess a patient's health status and identify any potential health problems. However, the acquisition and correlation of this information is generally a manual task that involves a healthcare provider undertaking initial assessment activities with rudimentary systems from which determinations about the diagnosis are made and/or additional tests may be undertaken. Accordingly, this process relies strongly on the expertise of the healthcare worker who may be inexperienced with some diseases/conditions, stressed, and/or otherwise not poised to provide optimal screening. As a result, the accuracy of the final diagnosis may be compromised, thereby causing unsatisfactory clinical outcomes due to corresponding treatments not being accurate.

SUMMARY

Systems, methods, and other embodiments relate to autonomous clinical screening and assessment using an imaging device controlled using a control model that implements reinforcement learning. In one or more arrangements, a present approach applies a symbiosis of neural networks to perform recognition and control of robotic systems when screening and assessing a patient. For example, the imaging device may be comprised of a robotic arm that articulates within proximity of a patient to position a camera or other imaging component to acquire imaging data of the patient. The camera may include a multifocal lens that can vary focus/magnification from a room-scale down to a microscopic scale by selecting different combinations of lenses. Accordingly, a control model functions to process information about a patient, such as previously acquired imaging data, and identify a location that is to be imaged. This determination can further include how to orient the imaging component and which combination of lenses to select in order to acquire the imaging data with desired characteristics (e.g., magnification and angle). As such, the system controls the imaging device to move into position and select the appropriate combination of lenses. A recognition model then processes the acquired imaging data to derive a determination about the condition of the patient.

This result may be a final determination or may be intermediate in that further information is to be acquired in order to fully assess the patient. Thus, the system may iteratively execute to acquire additional imaging data at different angles, magnifications, and, in one or more approaches, using different modalities (e.g., x-ray, MRI, etc.). In this way, the system can provide automated screening and assessment of a patient through autonomous control of the imaging device to acquire the imaging data, thereby improving the screening and assessment process overall.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. In some embodiments, one element may be designed as multiple elements, or multiple elements may be designed as one element. In some embodiments, an element shown as an internal component of another element may be implemented as an external component and vice versa. Furthermore, elements may not be drawn to scale.

FIG. 10A shows a clinical example of normal cells with focus points.

FIG. 10B shows a clinical example of cancer cells with assessment margins and clinical determents.

DETAILED DESCRIPTION

Figure 1:
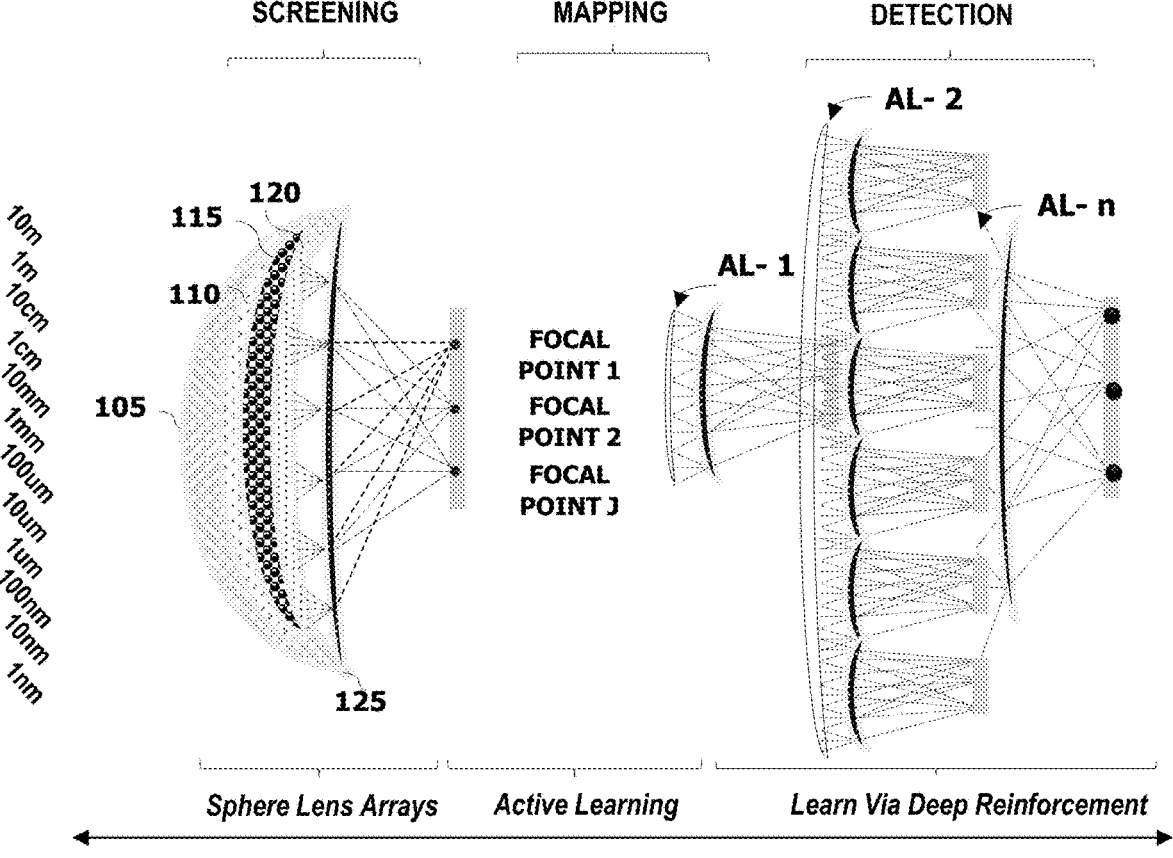
FIG. 1 is a diagram illustrating a process overview of the integration of the imaging device with reinforcement learning components.

Systems, methods, and other embodiments are disclosed associated with autonomous clinical screening and assessment using an imaging device controlled using a control model that implements reinforcement learning. In one or more arrangements, a present approach applies a symbiosis of neural networks to perform recognition and control of robotic systems when assessing a patient. For example, the imaging device may be comprised of a robotic arm that articulates within proximity of a patient to position a camera or other imaging component to acquire imaging data of the patient. In particular, the robotic arm may include multiple joints that provide for moving through six or more degrees of freedom to facilitate accurately positioning an imaging component or selection of imaging components, including a visible light camera, an infrared camera, an x-ray, an optical coherence tomography (OCT), an ultrasound, and so on. Moreover, the robotic arm may be mounted within a room of a medical facility or may be mobile and attached to a mobile base. In one aspect, the system that can image samples both inside and outside of the body, and it can be used to assess a wide range of biological parameters, such as cell morphology, tissue structure, and molecular composition.

By way of example, such as when a patient is suspected of having cancer of the colon, a provider may initiate the system, which determines that the patient's colon is to be imaged during a colonoscopy. This system can automatically choose the imaging modalities and parameters for the patient, and can also automatically process and analyze the images, including identifying and classifying any objects of interest, such as precancerous lesions or tumors. The provider then reviews the results from the system and makes a diagnosis, which may be based on a recommendation from the system. If the patient is diagnosed with cancer, the system can guide a surgeon during a minimally invasive procedure to remove a tumor. The system can also, in at least one approach, provide intraoperative visualization of cancerous tissues by either, at the bedside, imaging a resected specimen, or in vivo imaging a resection cavity. This functionality allows physicians to visualize, with microscopic precision, where cancer ends, thereby enabling the physician to accurately complete oncological surgeries and reduce reoperations. In addition, the system, in one arrangement, enables surgeons to better visualize critical structures in real-time. That is, nerves, blood vessels or other anatomical structures that are not easily visible (e.g., parathyroid glands, urethra, lymph node ducts, etc.) will be preserved because of improved awareness through the visualization, thus, sparing patients from long-term consequences and recovery. The system can also, in at least one arrangement, monitor the patient's response to treatment in real-time. This allows the doctor to adjust the treatment plan as needed, improving the patient's chances of a successful outcome.

Moreover, by way of an example involving a gastroscopy, a robotic mobile device equipped with a high-resolution camera and various imaging components can navigate within proximity of a patient, thereby providing a dynamic and precise view of the gastrointestinal tract. The device can, for example, switch between different imaging modes, such as visible light, infrared, optical coherence tomography, or multimodal imaging, including combining optical coherence tomography, reflectance confocal microscopy, and fluorescent microscopy, to aid in diagnosing conditions (e.g., ulcers, polyps, or cancer). The system automates the imaging process by, for example, automatically choosing the best imaging modalities and parameters for imaging the patient. Additionally, the system can also automatically process and analyze the images. The system also can combine multiple imaging modalities into a single endoscope, which allows providers to simultaneously image different aspects of the patient's anatomy, such as the structure of the tissue and the blood flow.

In an example of a medical facility, a mobile imaging robot featuring the system can be deployed. The robot can, for example, move autonomously from room to room, responding to imaging requests from healthcare professionals. This device can position imaging components like X-ray detectors, ultrasound probes and/or a multimodal microscope set with six or more degrees of freedom to capture detailed images for diagnostics. This flexibility allows for efficient use across various medical specialties.

In an example for emergency response, consider a situation in which a building collapses due to an earthquake. First, responders arrive on the scene and assess the situation. They determine that there are likely victims trapped inside, but the building is too unstable for them to enter safely. The autonomous portable imaging robot is deployed into the building. The robot uses integrated cameras and sensors to navigate through the debris and locate victims. The robot also uses various algorithms to assess the victims' injuries. The robot sends real-time images and data to the first responders outside the building. The first responders use this information to plan rescue and to provide the best possible care to the victims. Once the victims have been rescued, the robot can be used to help first responders visualize and localize trauma within the victims. This information can help first responders to provide more targeted and effective treatment.

As a further description of the system when integrated with a robot, a camera attached to the robot may include a multifocal lens that can vary focus/magnification from a room-scale down to a microscopic scale by selecting different combinations of lenses. Similarly, the other noted imaging components (e.g., OCT, etc.) may have imaging attributes associated with focus, magnification, and so on that a screening system controls. Accordingly, a control model functions to process information about a patient to determine how to arrange the imaging component to acquire imaging data for screening and assessment. The information may include previously acquired imaging data, preliminary imaging data, health information, and so on. From the information, the control model identifies a location to image. For example, the control model may initially acquire an image encompassing a broad view of the patient from which the screening system derives information, and the control model refines the location and characteristics of the imaging (e.g., angle, contrast agent specificity, field of view, image field of view, imaging resolution, imaging type, imaging time, specificity, sensitivity, and/or usability etc.).

For instance, in the context of cancer surgery, the provision of surgical margin information is important for the procedure's success. Surgical margin, in this context, refers to the distance between the tumor and the cut surface of the resected tissue specimen. The consensus among surgeons and radiation oncologists is that there should be no residual tumor present within a range of 1 to a maximum of 2 millimeters from the surface of the surgical specimen. The significance of achieving this margin is two-fold. Firstly, it significantly reduces the risk of tumor recurrence. When a positive margin, meaning tumor cells are still present in this critical margin zone, persists, there is a substantial risk of the cancer returning. This recurrence not only poses a threat to the patient's health but may also lead to compromised cosmetic outcomes. Ultimately, this could necessitate more extensive procedures, including mastectomy, as a last resort. Hence, achieving utmost precision and accuracy in ascertaining and preserving these surgical margins is imperative to optimize the results of cancer surgery. To aid in this critical task, this autonomous imaging device can be seamlessly introduced into the patient's body through a slender, flexible tube equipped with a camera at its tip. This scope is carefully guided through natural bodily orifices, such as the mouth or rectum. Positioned at the end of this scope is a microscope securely mounted, affording physicians a detailed view of the internal structures within the patient's body. Simultaneously, the system employs advanced technology to discern the boundary between normal and cancerous cells, thereby providing invaluable guidance during the surgical procedure.

Furthermore, imaging components integrated into various robotic systems offer versatile applications in the field of medical procedures. One such application involves employing miniature microscopes, which can be delicately inserted into a patient's body through a small incision. These microscopes are affixed to the robot, granting surgeons precise control over their movements within the patient's anatomy. This innovative approach enables surgeons to obtain highly detailed views of the surgical site without the necessity for extensive incisions.

In a different context, implantable imaging components serve as a continuous monitoring solution by capturing images of the surrounding tissue. This ongoing surveillance aids medical professionals in promptly identifying signs of diseases or infections.

Additionally, scope-based imaging components offer mobility within the patient's body, capable of independent movement after a small incision is made. This mobility is particularly valuable when imaging challenging-to-reach areas that are otherwise inaccessible with conventional microscopes.

Broadly, the determination by the control model includes, for example, how to orient the imaging component to capture a particular location on the patient. Furthermore, the determination also specifies settings/attributes for the imaging component, such as a combination of lenses to select for acquiring the imaging data with desired characteristics (e.g., magnification). As such, the system controls the imaging device to move into position and select the appropriate combination of lenses. A recognition model then processes the acquired imaging data to derive a determination about the condition of the patient. Thus, the control model and the recognition model function together to acquire and analyze data about the patient. In one configuration, the control model serves as a central command unit for a comprehensive range of imaging components, including autonomous multimodal microscopy sets, lens array sets, contrast labeling sets and/or marker sets. It provides seamless integration and precise control over these sophisticated technologies, enabling clinical screening and assessment autonomously.

This result may be a final determination or may be intermediate in that further information is to be acquired in order to fully assess the patient. Thus, the system may iteratively execute to acquire additional imaging data at different angles, magnifications, and, in one or more approaches, using different modalities (e.g., x-ray, MRI, etc.). That is, the screening system can provide the results from a prior acquisition to the control model, which then adjusts a focus point and acquires additional imaging data. The screening system may iterate the acquisition process in this manner until a condition of the patient is determined or according to another criteria. In this way, the screening system can provide automated clinical screening and assessment of a patient through autonomous control of the imaging device to acquire the imaging data, thereby improving the clinical screening and assessment process overall.

It should be further noted that the screening system, in at least one arrangement, actively learns how to improve the screening by implementing reinforcement learning with the control model. For example, the recognition model processes imaging data from the imaging device and provides results about what is depicted within the imaging data. The results may include, for example, a labeled version of the original imaging data according to a semantic segmentation representation of depicted areas. Thus, the result can specify locations and associated conditions with various areas of the patient. This may include identifying healthy areas and unhealthy and/or symptomatic areas on the patient from which a broader condition is assessed. Thus, the control model receives this information and determines a focus point, including a modality for imaging data capture and a configuration of attributes for subsequent imaging. As such, the results from the recognition model, i.e., identification of relevant areas, can serve as a reinforcement signal to train the control model about whether a focus point and other selections are appropriate or not. In this way, the screening system can intelligently learn how to best screen a patient according to observed aspects.

The present discussion will now provide an overview of relevant terms before turning to a further description of the screening system.

Terms

Autonomous Eyes (aEyes) is, in one approach, a computer vision system for medical sensing, which mimics human vision systems, using algorithms and robotic nanoscopy-microscope modules allowing aEyes to see and recognize disease, injury, and overall patient condition. aEyes, for example, is an algorithm based, outcome targeted, systems oriented, evidence driven (AOSE) autonomous system: 1. AI Algorithm-based: The system uses artificial intelligence algorithm sets to make decisions and take actions. 2. System-oriented: The system is, in one configuration, designed to operate as a whole, rather than as a collection of independent components. 3. Outcome targeted: The system is designed to achieve specific clinical outcomes, such as removing the cancerous tissue while preserving healthy tissue. 4. Evidence driven: The system is based on scientific evidence and clinical data.

In one approach, the presently described screening system may comprise one or more aspects of aEyes. aEyes is, in at least one arrangement, machine learning-based and can perform automated imaging tasks without human intervention. The screening system integrates aEyes to operate at different scales, from the nanoscale to the macroscopic scale, to visualize different objects and phenomena.

aEyes intelligent agents can include Contrast Agent Sets, aEyes labeling sets, aEyes marker Sets, aEyes signature sets, aEyes Lens Array Sets, and aEyes Multimodal Microscopy Sets can be used to make things more visible according to different purposes and properties.

In the field of healthcare, aEyes can be used to visualize and analyze biological samples and tissues, allowing for faster and more accurate diagnoses of diseases. For example, an aEyes implementation with an AI-powered nanoscope can capture high-resolution images of individual cells and structures of the cells as one modality of imaging, allowing for better understanding of cellular processes and disease mechanisms for assessment. Similarly, in one example, aEyes can include imaging components used to analyze tissue samples to detect cancerous cells, and a telescope to monitor the environment for pathogens or other health-related hazards.

The autonomous aspect of the screening system enabled by the control model and the recognition model provides for substantially continuous monitoring without human supervision, thereby reducing the need for manual labor and increasing the speed and accuracy of the analysis. This makes the screening system particularly useful in various settings, such as where large volumes of samples need to be analyzed quickly, such as in medical laboratories or environmental monitoring facilities.

aEyes medical image processing (aEyes-P), in one or more arrangements, includes a set of techniques and algorithms for analyzing and interpreting medical images or clinical video data to extract meaningful clinical information. The noted techniques/algorithms may include the following:

aEyes Medical Image Filtering: A process of modifying pixel values of an image to achieve a desired effect. Image filters may include smoothing filters, sharpening filters, and edge detection filters. Medical image filtering is a task in medical image processing, and AI autonomous methods can improve the efficiency and accuracy of this task. Some methods for medical image filtering are as follows:

Convolutional Neural Networks (CNNs): CNNs are a type of neural network that are used in image processing tasks, including medical image filtering. CNNs convolve a set of filters over an image and extract features at different levels of abstraction.

Recursive Neural Networks (RNNs): RNNs are another type of neural network. RNNs process an image in a recursive manner, where each pixel (or another data point) is processed based on previous values.

Support Vector Machines (SVMs): SVMs are a type of supervised learning algorithm that can be used for image filtering tasks. SVMs find the hyperplane that best separates different classes of pixels in an image.

Random Forests: Random forests are a type of ensemble learning algorithm that can be used for image filtering tasks. Random forests combine the output of multiple decision trees to make a final prediction.

Gaussian Filters: Gaussian filters are a type of linear filter used in medical image processing. These filters work by convolving an image with a Gaussian kernel to smooth out noise and other artifacts.

Median Filters: Median filters are a type of non-linear filter used in medical image processing. They work by replacing each pixel in an image with the median value of its neighboring pixels, which can help to reduce the impact of outliers and other noise.

aEyes Clinical Feature Extraction (aEyes-F) is a process of identifying distinctive features in an image or video, such as corners, edges, blobs, or lines. Some methods that are used in aEyes clinical feature extraction include:

CNNs are a type of neural network that can be used for clinical feature extraction. CNNs can be trained to extract relevant features from medical images, such as tumors or lesions, which can then be used as input for further analysis.

RNNs are another type of neural network that can be used for clinical feature extraction. RNNs are particularly useful for processing time-series data, such as electrocardiograms (ECGs) or electroencephalograms (EEGs).

Principal Component Analysis (PCA): PCA is a technique for reducing the dimensionality of a dataset by identifying the most important features. PCA can be used for clinical feature extraction by identifying the most relevant features in a dataset of clinical measurements.

Independent Component Analysis (ICA): ICA is another technique for reducing the dimensionality of a dataset by identifying the independent sources of variation. ICA can be used for clinical feature extraction by identifying the underlying sources of variation in a dataset of clinical measurements.

SVMs are a type of supervised learning algorithm that can be used for clinical feature extraction. SVMs find the hyperplane that best separates different classes of patients based on their clinical features.

Random forests are a type of ensemble learning algorithm that can be used for clinical feature extraction. Random forests combine the output of multiple decision trees to make a final prediction about a patient's clinical features.

aEyes Object Recognition (aEyes-R) is a process of detecting and classifying objects within an image or video. Object recognition algorithms typically involve machine learning techniques, such as deep learning. Some methods that are used in aEyes clinical object recognition include:

Convolutional Neural Networks (CNNs): CNNs are a type of neural network that can be used for object recognition in medical images. CNNs can be trained to recognize different types of objects in medical images, such as tumors or organs.

Region-Based Convolutional Neural Networks (R-CNNs): R-CNNs are a type of neural network that can be used for object recognition in medical images. R-CNNs work by first generating region proposals in an image and then classifying each region proposal using a CNN.

Faster R-CNNs: Faster R-CNNs are an extension of R-CNNs that can perform object recognition more quickly. Faster R-CNNs work by sharing computation across region proposals, which allows them to process images more efficiently.

You Only Look Once (YOLO): YOLO is a type of neural network that can perform object recognition in real-time. YOLO works by dividing an image into a grid and predicting the class and location of objects within each grid cell.

Mask R-CNNs: Mask R-CNNs are a type of neural network that can perform object recognition and segmentation in medical images. Mask R-CNNs work by generating region proposals, classifying each region proposal, and then generating a binary mask for each object within the region proposal.

Deep Belief Networks (DBNs): DBNs are a type of neural network that can be used for object recognition in medical images. DBNs work by learning a hierarchical representation of features in an image, which can then be used to recognize different types of objects.

Haar cascades: Haar cascades are a type of machine learning-based object detection algorithm that can be used for clinical object recognition. Haar cascades work by training a classifier to detect specific features, such as edges or corners, in an image.

Scale-Invariant Feature Transform (SIFT): SIFT is a feature detection algorithm that can be used for object recognition in medical images. SIFT works by detecting key points in an image and then describing the local image structure around each key point.

Local Binary Patterns (LBP): LBP is another feature detection algorithm that can be used for object recognition in medical images. LBP works by comparing the pixel values of a central pixel with its neighbors to create a binary pattern that can be used to describe local image structure.

aEyes Motion Analysis (aEyes-M): A process of tracking the movement of objects within an image or video. Motion analysis techniques can be used to detect and track moving objects, estimate velocity and direction, and analyze behavior. Some methods that are used in aEyes medical motion analysis:

Optical flow: Optical flow is a technique for analyzing the motion of objects in an image sequence. Optical flow can be used for medical motion analysis by tracking the motion of organs or tissues in medical images over time.

Lucas-Kanade method: The Lucas-Kanade method is a technique for estimating optical flow that is particularly useful for tracking small movements over short time periods. The Lucas-Kanade method can be used for medical motion analysis by tracking the motion of organs or tissues in medical images, such as echocardiograms or MRI scans.

Convolutional Neural Networks (CNNs): CNNs can also be used for medical motion analysis by analyzing video sequences of medical images. CNNs can be trained to recognize specific types of motion, such as abnormal gait patterns or abnormal heart contractions.

Kalman filters: Kalman filters are a type of recursive filter that can be used for motion analysis in medical data. Kalman filters work by estimating the state of a system based on noisy measurements over time. Kalman filters can be used for medical motion analysis by tracking the motion of organs or tissues in medical images, such as ultrasound or MRI scans.

Hidden Markov Models (HMMs): HMMs are a type of statistical model that can be used for motion analysis in medical data. HMMs work by modeling the probability of a sequence of observations based on a hidden sequence of states. HMMs can be used for medical motion analysis by analyzing video sequences of medical images, such as endoscopic or laparoscopic procedures.

aEyes Segmentation: A process of dividing an image or video into segments or regions based on defined characteristics, such as color, texture, or shape. Some methods that may be used in aEyes medical segmentation include:

Convolutional Neural Networks (CNNs): CNNs are a type of neural network that can be used for medical image segmentation tasks. CNNs can be trained to segment specific regions of interest, such as tumors or organs, within medical images.

U-Net: U-Net is a deep learning-based segmentation algorithm used in medical image analysis. U-Net works by combining a contracting path, which captures contextual information, with an expansive path, which enables precise localization of objects.

Random Walker: The random walker algorithm is a segmentation method used in medical image analysis. Random walker works by computing a probability distribution of paths from each pixel to a set of seed points, and then using this distribution to segment the image.

Region growing: Region growing is a simple but effective method for medical image segmentation. Region growing works by starting from a seed point and expanding the region by adding neighboring pixels that meet certain criteria.

Fully Convolutional Networks (FCNs): FCNs are another type of neural network that can be used for medical image segmentation. FCNs work by performing convolution operations across the entire image to generate a pixel-wise segmentation mask.

Region-Based Segmentation: Region-based segmentation is a technique that involves identifying regions of interest within medical images and then segmenting them. This technique may be used in medical data analysis, such as detecting and segmenting tumors in MRI scans.

Active Contour Models: Active contour models, also known as snakes, are a type of algorithm that can be used for medical image segmentation. Active contour models work by defining a contour around the object of interest and iteratively adjusting the contour to fit the object's boundaries.

Graph Cuts: Graph cuts are a type of algorithm that can be used for medical image segmentation. Graph cuts work by dividing an image into regions and then iteratively adjusting the boundaries between the regions to find the best segmentation.

aEyes Stereo Vision is, in one embodiment, the process of extracting 3D information from multiple 2D images of a scene and may include medical image analysis for tasks, such as depth estimation and 3D reconstruction. Some aEyes methods used for medical stereo vision include:

Stereo Matching: Stereo matching is a technique that involves finding corresponding points in two or more 2D images of a scene. This can be done using various algorithms, such as block matching, semi-global matching, and deep learning-based methods. Stereo matching can be used to estimate depth maps of medical images, such as CT or MRI scans.

Deep Learning-based methods: Deep learning-based methods have recently been applied to stereo vision in medical imaging, particularly for tasks such as 3D reconstruction and object segmentation. These methods involve training neural networks to learn the mapping between stereo pairs and depth information.

Point cloud generation: Point cloud generation involves using the depth information obtained from stereo vision to generate a 3D point cloud of the scene. This technique is used in medical imaging, such as generating 3D models of organs or tissues from CT or MRI scans.

Structure from Motion (SfM): SfM is a technique that involves reconstructing 3D structures from multiple 2D images of a scene. SfM can be used to estimate the 3D structure of medical images, such as X-ray or endoscopy images. SfM can be performed using various algorithms, such as bundle adjustment and incremental reconstruction.

Depth Estimation Networks: Depth estimation networks are deep learning-based methods that can be used to estimate depth maps from stereo image pairs or monocular images trained according to SfM. These networks may be trained on large datasets of annotated stereo images and can be used for tasks such as 3D reconstruction and image-based navigation.

Multi-View Stereo: Multi-view stereo is a technique that involves estimating depth maps from multiple images of a scene. This can be done using various algorithms, such as patch-based methods and graph-cut-based methods. Multi-view stereo can be used for tasks such as 3D reconstruction and surface modeling.

Visual Odometry: Visual odometry is a technique that involves estimating the motion of a camera based on image sequences. Visual odometry can be used to estimate the motion of medical imaging devices, such as endoscopes, and can be used for tasks such as navigation and localization.

Feature matching: Feature matching is a technique that involves identifying the same features in two or more images and using their position to infer depth information. This technique can be used in conjunction with stereo matching to improve the accuracy of depth estimation.

aEyes Algorithms for the analysis of multi-modal (2D, 3D, 4D, and/or multiple channels) microscopy imaging data: Multi-modal microscopy imaging data refers to images captured using different imaging modalities, such as fluorescence, confocal, and electron microscopy, among others. Algorithms that can handle multi-modal imaging data are used for analyzing these types of data. Some algorithms used for the analysis of multi-modal microscopy imaging data include registration, segmentation, and feature extraction. Image registration algorithms align images from different modalities to a common coordinate system, enabling a direct comparison of images. Segmentation algorithms separate the image into regions of interest based on predefined criteria, such as intensity, shape, or texture. Feature extraction algorithms extract relevant features from the segmented regions, such as shape, texture, or intensity values.

Machine learning of reconstruction, classification, detection, registration, or dense segmentation of images obtained by microscopy modalities: Machine learning algorithms can be trained to perform various image processing tasks, such as reconstruction, classification, detection, registration, or segmentation. Reconstruction algorithms can be trained to reconstruct high-quality images from low-quality or incomplete imaging data, such as those obtained from electron microscopy. Classification algorithms can classify images into different categories, such as diseased or healthy cells. Detection algorithms can detect and localize specific objects, such as nuclei or proteins, within an image. Registration algorithms can align images acquired using different imaging modalities or at different time points. Dense segmentation algorithms can segment images into multiple regions with high accuracy.

Automated analysis of big microscopy data, including phenotyping, diagnosis, atlasing, rare event detection, tracking, shape analysis, and spatial analysis: The increasing availability of big microscopy data requires automated image analysis methods to extract relevant information from the data. Automated analysis methods can analyze large datasets quickly and accurately, providing insights that would be difficult to obtain manually. Automated analysis methods can perform various tasks, such as phenotyping, diagnosis, atlasing, rare event detection, tracking, shape analysis, and spatial analysis. Phenotyping involves measuring morphological and functional features of cells or tissues to determine their phenotype. Diagnosis involves identifying diseases or abnormalities from microscopy images. Atlasing involves creating a comprehensive map of the cellular and molecular architecture of an organism or tissue. Rare event detection involves identifying rare events, such as cancer cells, within a large dataset. Tracking involves following objects, such as cells, over time within an image sequence. Shape analysis involves quantifying the shape of objects within an image, such as the morphology of neurons. Spatial analysis involves analyzing the spatial relationships between objects within an image, such as the location of blood vessels within a tissue.

Autonomous Eyes Live-cell Imaging (aEyes-LI) combines robotics and live-cell imaging to automate the process of identifying and tracking cells and their behavior in real-time. This technology involves the use of specialized robotic systems that are equipped with advanced microscopy and imaging systems (e.g., as a modality of the imaging component of the imaging device), as well as algorithms that enable the identification and tracking of individual cells. For example, it can be used to study the behavior of cancer cells and the effects of potential cancer drugs on those cells. It can also be used to study the development of embryos and the effects of genetic mutations on embryonic development. Some components of autonomous robotic live-cell imaging recognition include:

Autonomous Eyes Microscopy and Imaging Systems (aEyes-IS) are specialized microscopes and imaging systems that are designed to capture high-quality images of living cells in real-time. These systems may include fluorescence microscopy, confocal microscopy, and other advanced imaging technologies.

Selective Optical Imaging Combination (aSOIC): aSOIC can provide a more comprehensive view of tissues than any one technique alone. For example, FM can be used to label specific molecules or structures in cells or tissues, while OCT and RCM can be used to create high-resolution images of the surrounding tissue. This combination of techniques can be used to improve the diagnosis and treatment of a variety of diseases, Fluorescent Microscopy (FM) uses fluorescent dyes to label specific molecules or structures in cells or tissues. This allows for the visualization of specific structures, such as cell nuclei, mitochondria, and blood vessels. has a high resolution, but it has a limited penetration depth. This makes it ideal for imaging thin tissues, such as the skin or the cornea. OCT has a greater penetration depth than FM, but it has a lower resolution. This makes it ideal for imaging thicker tissues, such as the retina or the muscles. RCM has a high resolution, but it has a limited penetration depth. This makes it ideal for imaging thin tissues, such as the skin or the cornea.

Optical Coherence Tomography (OCT) uses the interference of light to create images of tissues with a resolution of micrometers to millimeters. OCT has a greater penetration depth than FM, typically up to a few millimeters. However, the resolution of OCT is not as high as FM. FM uses fluorescent dyes to label specific molecules or structures in cells or tissues. The fluorescent dyes are excited by light of a specific wavelength, and they emit light of a different wavelength. This emitted light can be detected and used to create an image of the labeled molecules or structures.

Reflectance Confocal Microscopy (RCM) is a type of confocal microscopy that uses a focused laser beam to create images of tissues with a high resolution, typically up to a few micrometers. RCM has a limited penetration depth, typically only a few hundred micrometers. RCM is a type of confocal microscopy that uses a focused laser beam to create images of tissues with a high resolution, typically up to a few micrometers. RCM works by scanning the laser beam across the tissue and detecting the reflected light. The reflected light is then used to create an image of the tissue structure.

Contrast Labeling Types: The best contrast labeling type to use depends on the specific application.

Brightfield: This is the simplest type of contrast labeling, and it does not require any special dyes or stains. Brightfield microscopy works by exploiting the natural differences in light absorption and scattering by different cells and tissues. By choosing the right contrast labeling type for the specific application, scientists can gain valuable insights into the structure and function of cells and tissues.

Darkfield: This type of contrast labeling uses a special condenser and objective lens to create a dark background. This makes cells and tissues appear brighter and easier to see.

Phase contrast: This type of contrast labeling uses the interference of light to create images of cells and tissues. Phase contrast microscopy is particularly useful for imaging living cells, as it does not require any dyes or stains that could damage the cells.

Differential interference contrast (DIC): DIC is a type of phase contrast microscopy that uses two polarizing filters to create images with enhanced contrast. DIC is particularly useful for imaging thick tissues, as it can provide a three-dimensional view of the sample.

Fluorescence: This type of contrast labeling uses fluorescent dyes to label specific molecules or structures in cells or tissues. The fluorescent dyes are excited by light of a specific wavelength, and they emit light of a different wavelength. This emitted light can be detected and used to create an image of the labeled molecules or structures.

Immunohistochemistry (IHC): This type of contrast labeling uses antibodies to label specific proteins in cells or tissues. IHC is a powerful tool for research and diagnostics, as it can be used to identify specific cell types and disease markers.

In situ hybridization (ISH): This type of contrast labeling uses RNA probes to label specific genes in cells or tissues. ISH is a powerful tool for research, as it can be used to study gene expression and to identify genetic mutations.

Electron microscopy: Electron microscopy uses a beam of electrons to create images of cells and tissues. Electron microscopy can provide very high-resolution images, but it is a complex and expensive technique.

Robotic systems are robotic systems that are designed to move the microscope and imaging system to the location of the subjects being studied.

Artificial intelligence algorithms are computer algorithms that are designed to analyze the images captured by the imaging system and identify individual cells based on their characteristics, such as shape, size, and movement. These algorithms may also be used to track the movement and behavior of individual cells over time. For example, live cancer cell imaging recognition is the process of analyzing live images of cancer cells and identifying them based on their characteristics and features. This can be done using various techniques such as machine learning, computer vision, and deep learning.

The first step in live cancer cell imaging recognition is to acquire high-quality images of the cells using advanced imaging technologies such as fluorescence microscopy, confocal microscopy, or multiphoton microscopy. These images can then be preprocessed to remove noise and enhance the quality of the images.

Next, the images are fed into an algorithm that uses machine learning or deep learning techniques to analyze the images and identify cancer cells. This algorithm can be trained using a large dataset of annotated images of cancer cells to learn the characteristic features of cancer cells, such as their shape, size, texture, and intensity.

Once the algorithm has been trained, it can be used to analyze live images of cancer cells in real-time and identify cancer cells with high accuracy. This can be used for various applications such as cancer diagnosis, drug discovery, and monitoring the effectiveness of cancer treatments.

Autonomous Eyes System of systems (aEyesS) is, in one approach, an AI-based medical sensing set of systems or system elements that interact to provide a unique capability that none of the constituent systems can accomplish on its own. Systems elements can be necessary to facilitate the interaction of the constituent systems in the system of systems with lens array nanoscope-microscope for real-time robotic perception of disease, injury, and overall patient condition by leveraging a series of algorithms, robotic widefield-narrow field imaging modules, and deep reinforcement learning-based adaptive controllers to process comprehensive data to improve accuracy, speed, and efficiency for complex diagnoses and therapeutic treatments and continually learn and improve performance over time.

Autonomous Eyes Constituent Systems (aEyesC) can be part of one or more aEyesS. Each constituent interacts within the aEyesS to provide the unique capability of the aEyesS.

aEyes with 3D-light field, light sheet, and volume electron microscopy perform imaging and analyzing biological samples at the cellular and molecular levels. 3D-light field microscopy uses a microlens array to capture information about the direction and intensity of light rays at different points in a three-dimensional space. This allows for the reconstruction of a 3D image with depth information.

Light sheet microscopy is a technique that uses a thin sheet of light to selectively illuminate a specific plane of a sample. This reduces phototoxicity and photobleaching, allowing for longer imaging times and better preservation of sample integrity. It also allows for the rapid acquisition of high-resolution images, making it ideal for live-cell imaging. Autonomous 3D nanodynamics microscopy is a novel technique that combines several advanced technologies to enable high-resolution, real-time imaging of nanoscale structures in three dimensions. In summary, autonomous 3D nanodynamics microscopy is a powerful technique that combines advanced technologies to enable high-resolution, real-time imaging of nanoscale structures in three dimensions. It has many potential applications in a wide range of fields, from materials science to biophysics. Aspects of this technique, include:

aEyes Nanopositioning uses advanced nanopositioning systems to manipulate the position of the sample and the imaging probe with high precision. These systems typically use piezoelectric actuators to move the sample or the probe in the x, y, and z directions.

aEyes Scanning probe: Autonomous 3D nanodynamics microscopy uses a scanning probe microscope (SPM) to image the sample. SPM can achieve high-resolution images by scanning a sharp probe over the surface of the sample, measuring the forces between the probe and the surface. This technique can produce images with sub-nanometer resolution.

Fast data acquisition: To enable real-time imaging of nanoscale dynamics, autonomous 3D nanodynamics microscopy uses fast data acquisition and processing techniques. These include fast detectors, high-speed data acquisition cards, and real-time signal processing algorithms.

aEyes control algorithms: To enable autonomous operation, the technique uses advanced control algorithms that can adjust the position of the sample and the probe in real-time based on the acquired data. These algorithms can also optimize the scanning parameters to minimize the measurement time and maximize the image quality.

Volume electron aEyes uses focused ion beams to slice a sample into extremely thin sections, which are then imaged using electron microscopy. This allows for the visualization of ultrastructural details with nanometer resolution, making it an important tool for studying the fine structure of cells and tissues. For example, aEyes may enable visualizing samples precisely and confidently in 3D.

aEyesS involves coordination of hardware and software, (robot eyes and AI deep reinforcement learning) to function. This Autonomous Eyes use of lens arrays in microscopes such as holographic, light field and light sheet microscopy allows for parallel imaging of multiple regions of interest within a sample, providing high-throughput imaging capabilities. When combined with robotics and AI technologies, these microscopes and other imaging components can automate many aspects of the imaging process, including sample preparation, stage movement, and 3D-widefield-narrowfield image acquisition. The robot vision uses algorithms to identify, distinguish and classify objects by size, color, and other attributes, and to discover and interpret patterns in visual data, such as photos, videos, cross-modal data, and multi-modal data.

aEyesS combines visual data at all scales from nano to macro and has the advantage of being able to potentially identify double or multiple infections caused by more than one virus and bacteria, which could be missed by molecular or antigen tests. Moreover, the nature of the samples to be analyzed can be diverse, from body fluids or biopsies analyzed directly or after cell culture.

aEyes Deep Reinforcement Learning-Based Adaptive Controller (aEyes-DRL-BAC): Deep Reinforcement Learning (DRL) combines reinforcement learning with deep neural networks to enable autonomous eyes to learn from experiences in complex environments. In the context of control systems, a DRL-based adaptive controller is a type of control system that uses DRL to learn and adapt to changing conditions in real-time. The controller uses DRL to train a deep neural network to map the state of a system to an optimal control policy. The controller continually updates its policy as it receives new data from the system via, for example, a reward signal, allowing it to adapt to changing conditions and improve its performance over time.

Medical Sensing is the use of sensors and devices to monitor various aspects of human health and medical conditions. This includes sensors for measuring biological signals, such as heart rate, blood pressure, and blood glucose levels, as well as sensors for imaging the body, such as X-rays, CT scans, and MRI machines. Medical sensing has revolutionized the field of medicine by providing new and more effective ways to diagnose and treat medical conditions. For example, medical imaging sensors can help physicians to visualize the internal structure of the body to diagnose diseases and plan treatments.

aEyes Medical Robotic Sensing is the sub-area of robotics that implements sensing capabilities so that the aEyes are more human-like. Robotic sensing gives the aEyes the ability to see, touch, hear, and move, and it uses algorithms that use environmental feedback. aEyes uses Robot Sensors including, for example, ultrasonic, temperature, humidity, force, and so on. Robotic sensors are used to estimate the robot's condition and environment; these signals are passed to the controller to enable the appropriate behavior.

The sensors may include sensors that measure physical quantities, such as speed or pressure and converts the measured quantities into a signal, which can be measured electrically. The sensors provide analogs to the human senses to monitor phenomena for which the humans lack explicit sensors, and they can measure physical properties, such as the distance between the objects. The sensors can measure the presence of light and the frequency of sound, they can measure the object proximity, they can measure the presence or the absence of the object, bearing, the color, and the distance between the objects. The sensors can measure the physical orientation and the coordinates of the object in the space, and they can measure the heat, the wavelength of infrared or ultraviolet rays, the temperature, the magnitude, and the direction. The sensors can measure the presence and concentration of chemicals or reactants, and they can measure the presence, color, and intensity of light, they can measure the presence, frequency, and intensity of sound.

Autonomous medical image processing refers to the use of machine learning algorithms to automate the process of analyzing and manipulating digital images. Types of AI autonomous image processing techniques:

Image recognition: AI algorithms can be trained to recognize specific features within an image, such as objects, patterns, or text. This can be used for tasks such as identifying tumors in medical images or recognizing faces in security footage.

Image segmentation: AI algorithms can be used to segment an image into different regions or objects. This can be used for tasks such as separating foreground and background in images or identifying individual cells in microscopy images.

Image restoration: AI algorithms can be used to restore degraded or low-quality images by filling in missing pixels or removing noise. This can be used for tasks such as restoring damaged historical photographs or improving the resolution of satellite imagery.

Image synthesis: AI algorithms can be used to synthesize new images that are similar in style or content to existing images. This can be used for tasks such as generating realistic 3D models from 2D images or creating artistic renderings of photographs.

Autonomous Eyes (aEyes) for Robotic Macro-Micro-Nano scale clinical measurement: dimensions: macro, micro, nano, and soluble nanobiotechnology. Examples of variations in configurations with new terminologies for each extension Macro: Cell, Stem cell & tissue encapsulation; cell, stem cell & tissue in scaffold; membrane coated bio adsorbent for hemoperfusion. Micron: synthetic cells, microcapsules, microparticles microspheres, insert genes into cells, replicating synthetic cells; Mamo: Nanoparticles, nano capsules, liposomes, polymer some, nanotubule; nano-soluble complex: polyproteins, PEG-protein, nanotherapeutics, and so on.

3D-widefield-narrow field (3-WNF) imaging technology is a type of imaging technology that combines widefield and narrow-field imaging techniques to provide detailed, high-resolution 3D images of samples and objects. In widefield microscopy, the entire sample is illuminated at once and the image is captured using a single camera. This technique provides a quick and easy way to visualize a sample, but it can be limited in terms of resolution and depth of field. In contrast, narrow-field microscopy uses a tightly focused laser to illuminate a small area of the sample, which is then imaged using a high-resolution camera. This technique provides high-resolution images, but it can be time-consuming and requires scanning the sample one point at a time. 3D-widefield-narrow field microscopy combines the strengths of both techniques by using a widefield illumination source to quickly visualize the sample and a narrow field laser to capture high-resolution images of specific regions of interest. This allows for a fast and efficient way to capture 3D images with high resolution and a wide field of view.

AI-3D-wide-field narrow-field microscopy measurement technology refers to the integration of machine learning algorithms into 3D-wide-field narrow-field microscopy systems to improve the accuracy and efficiency of measurements and image analysis. By using machine learning algorithms, these microscopes can automatically identify and track specific features in the images, such as cells, organelles, or particles, and perform quantitative measurements on these features. This can greatly reduce the time and effort required for manual measurements and can provide more accurate and consistent results. In addition, AI algorithms can also be used to analyze the images and identify patterns and relationships that might be difficult for a human observer to see. This can lead to new insights and understanding of complex structures and processes. Overall, the integration of AI into 3D-widefield-narrow field microscopy measurement technology provides a powerful tool for to provide detailed, high-resolution images and measurements of objects.

Real-time direct AI 3D-widefield-narrow field screen and measurement refers to the use of advanced imaging and AI technologies to provide real-time, high-resolution 3D images and measurements of samples and objects. In real-time direct AI 3D-widefield-narrow field screen and measurement, the microscope captures 3D images of a sample and analyzes the images in real-time using AI algorithms.

This allows for rapid and efficient measurement and analysis of the sample, without the need for time-consuming post-processing. The AI algorithms can perform a variety of functions, such as automatically identifying and tracking specific features in the images, such as cells, organelles, or particles, and performing quantitative measurements on these features. This can greatly reduce the time and effort required for manual measurements and can provide more accurate and consistent results. In addition, the AI algorithms can also be used to analyze the images and identify patterns and relationships that might be difficult for a human observer to see.

3D measurement, the microscope captures images of an object from multiple angles and then uses computer algorithms to combine these images into a 3D model that can be rotated and viewed from any angle. This allows for precise measurement of features and dimensions in three dimensions.

3D Body Scan for Made-to-Measure: To reliably detect physical changes, high-precision 3D anthropometric data must be captured. Body measurements add tangible value if they meet the highest quality standards. Autonomous Eyes provide a powerful tool for detailed observation and measurement of a wide range of samples and objects, allowing for greater insight and understanding of complex structures and processes.

Autonomous Hybrid Microscope (aHM) that combines 3D, light sheet, and light field technologies is a highly advanced imaging tool that utilizes artificial intelligence (AI) to perform tasks such as image analysis and experiment control without human intervention. This type of microscope provides a unique combination of capabilities for capturing high-resolution images of biological samples in three dimensions, while also offering the benefits of automation, including increased efficiency and accuracy. The 3D, light sheet, and light field technologies provide a complete understanding of the structure of biological samples, enabling researchers to study the relationships between cells and tissues in all three dimensions. The use of AI algorithms for image analysis and experiment control can greatly enhance the accuracy and efficiency of data collection and analysis, making it possible to perform complex experiments with minimal human intervention.

The components of an autonomous hybrid microscope that combines 3D, light sheet, and light field technologies may include:

Light source: A highly stable and uniform light source, such as a laser, is used to illuminate the biological sample.

Imaging optics: A set of high-resolution imaging lenses and filters, as well as a beam splitter, are used to capture and process the light passing through the sample.

Camera: A high-resolution camera sensor, such as a scientific-grade CCD or CMOS sensor, is used to capture images of a sample.

Light sheet generator: A specialized component that creates a thin sheet of light that is used to illuminate the sample in a controlled and gentle manner.

Light field technology: A set of optical components, such as micro lenses or a camera array, that are used to capture and process the light field information from the sample.

Microlens arrays are one, two, three-dimensional arrays of microlenses, i.e., rather small lenses (lenslets). In various arrangements, the lenslets form a periodic pattern either of square or hexagonal type as further shown in subsequent figures, where the lens pitch is, for example, a few hundred micrometers, some tens of micrometers or even less.

The outer transverse shape may be a square (e.g., 10 mm×10 mm), a rectangle, or a circle. The number of microlenses can vary depending on the implementation. For example, the number of lenses may be thousands, or more (e.g., millions). The lenses may include anti-reflection coatings on both sides. The lenses may be realized as a thin transparent structured layer contacted to a flat homogeneous glass or semiconductor substrate. The microlens array may be a part of a larger assembly. For example, some CCD and CMOS image sensors contain one microlens per photodetector for increasing the light collection efficiency: all incident light should be concentrated to the active areas, which cover only part of the chip area.

Multiple layers of lens array are, for example, composed of multiple individual lenses arranged in a regular pattern. The number and arrangement of lenses in the array can vary depending on the intended application. The lens array may include multiple layers, which can be characterized as follows:

The substrate layer: This is the bottom layer of the lens array and provides a base on which the lenses can be mounted. The substrate layer can be made of a variety of materials, such as glass or plastic.

The spacer layer: This layer is typically composed of a material that is optically transparent and provides a fixed distance between the substrate layer and the lens layer. The thickness of the spacer layer is critical in determining the focal length of the lenses.

The lens layer: This is the top layer of the lens array and consists of multiple individual lenses arranged in a regular pattern. Each lens focuses light onto a specific point, and the combination of lenses in the array can be used to form a larger image.

The number of layers in a lens array can vary depending on the specific application. For example, some lens arrays may only have one layer of lenses, while others may have multiple layers to increase the resolution and magnification of the images.

Parameters of the Microlens Arrays can differ in a number of respects:

The lenses may be of a circular type, but there are also arrays with cylindrical lenses. Note that even lenses focusing on both directions can have a square geometrical shape.

They may be optimized for different spectral ranges, for example, for visible light and/or parts of the near-infrared. This affects the choice of optical material and the anti-reflection coatings.

Different values of the lens pitch are available—from a few micrometers (only a few times an optical wavelength!) to hundreds of micrometers.

In many cases, a large fill factor is desirable. This refers to the ratio of the total area of usable lens apertures to the total area of the array. For example, for a square array of circular lenses without any space between those, the fill factor would be $\pi/4 \approx 78.5\%$. Hexagonal arrays can reach a higher fill factor but are not usable for all applications.

Each lens is characterized by a diameter and focal length. The homogeneity of the focal length over the full device area can be important. For imaging applications, the number of optical aberrations can also be relevant. In some cases, one uses aspheric lenses (e.g., made with reactive ion etching) for minimizing aberrations.

The light throughput is limited by the fill factor and possibly by non-perfect transmissivity of the lenses due to parasitic absorption and/or reflections.

Clinical Assessment-Diagnostics-Treatment Precise Measurement:

Clinical screening and assessment are preliminary processes aimed at identifying individuals who may be at risk of a particular condition or disease. It is used to determine whether further evaluation or assessment is necessary. The primary outcome of clinical screening and assessment is to determine whether further evaluation or assessment is needed. Those who screen positive are referred for a more comprehensive clinical assessment. Examples of clinical screening and assessment include newborn clinical screening and assessment for genetic disorders, mammography for breast cancer clinical screening and assessment, or depression questionnaires administered in primary care settings.

Clinical Assessment: Clinical assessment is a comprehensive and in-depth evaluation of an individual's physical, mental, or emotional health. It aims to diagnose and understand the nature and severity of a condition or illness. The outcome of an assessment is a diagnosis, a detailed understanding of the individual's condition, and, if necessary, a treatment plan. It informs clinical decision-making. Examples of clinical assessment include a comprehensive physical examination by a physician, a psychological assessment by a psychologist, or a diagnostic imaging study (e.g., MRI or CT scan) to assess a specific medical condition.

Autonomous lens array microscope (ALAM) is a type of microscope that uses an array of lenses and advanced algorithms to automatically capture high-resolution images of biological samples. ALAMs are designed to be compact, easy to use, and capable of producing high-quality images without the need for specialized expertise or manual adjustments.

The components of an ALAM include a lens array, a light source, a camera, and, for example, an AI-powered image processing system. The lens array is typically composed of hundreds or thousands of tiny lenses, each of which captures a small portion of the sample. The light source illuminates the sample, and the camera captures multiple images of the sample, each from a slightly different angle. The AI-powered image processing system then uses advanced algorithms to combine the images into a single high-resolution image.

The advantages of ALAMs include their compact size, ease of use, and ability to capture high-resolution images quickly and automatically. They also have the potential to significantly reduce the cost and complexity of microscopy, making it more accessible to a wider range of researchers and clinicians.

Applications of ALAMs include biological and medical imaging, where they can be used to capture high-resolution images of cellular and tissue structures. They can also be used in industrial and manufacturing settings, where they can be used for quality control and defect detection.

Nanoscope and microscope: Optical imaging with nanoscale resolution and a large field of view is highly desirable in many areas. An objective lens with a low numerical aperture (NA) has a large field of view but poor resolution. In contrast, a high NA objective lens will have a higher resolution but reduced field of view. In an effort to close the gap between these trade-offs, the system implements an acoustofluidic scanning nanoscope (AS-nanoscope) that can simultaneously achieve high resolution with a large field of view. The AS-nanoscope relies on acoustofluidic-assisted scanning of multiple microsized particles. A scanned 2D image is then compiled by processing the microparticle images using an automated big-data image algorithm.

aEyes Endoscopy Set (aES) is a type of microscope that is used to image objects inside the body. aES is a type of endoscope that uses artificial intelligence (AI) to automate the imaging process. This means that the system can automatically choose imaging modalities and parameters suited for the patient, and it can also automatically process and analyze the images. aES combines multiple imaging modalities into a single endoscope. This allows doctors to simultaneously image different aspects of the patient's anatomy, such as the structure of the tissue and the blood flow. This can help to better understand the underlying pathology of a disease and to make more informed determination.

Stimulated emission depletion (STED) microscopy is one of the techniques that make up super-resolution microscopy. It creates super-resolution images by the selective deactivation of fluorophores, minimizing the area of illumination at the focal point, and thus enhancing the achievable resolution for a given system. STED microscopy is one of several types of super-resolution microscopy techniques that have recently been developed to bypass the diffraction limit of light microscopy and to increase resolution. STED is a deterministic functional technique that exploits the non-linear response of fluorophores aEyes used to label biological samples in order to achieve an improvement in resolution, that is, STED allows for images to be taken at resolutions below the diffraction limit. This differs from the stochastic functional techniques such as Photoactivated localization microscopy (PALM) and stochastic optical reconstruction microscopy (STORM) as these methods use mathematical models to reconstruct a sub-diffraction limit from many sets of diffraction-limited images.

Autonomous Microbiology (aM): is an aEyes analysis of the structure and function of microbial groups, the interrelationships and mechanisms of internal communities, and the relationships between microorganisms and their environments or hosts.

Autonomous microbiome is an aEyesic collection of all microbial species and their genetic information and functions in a given environment. an aEyes analysis of the microbiome also includes the interaction between different microorganisms, the interaction between microorganisms and other species, and the interaction between microorganisms and the environment.

Volume electron microscopy (vEM) is a collection of techniques that use electron microscopy to image structures in three dimensions. In summary, each vEM technique has its strengths and limitations, and the choice of technique depends on the specific sample and research question. SBEM and FIB-SEM are useful for imaging large volumes, while TEM tomography and ssTEM provide high resolution at the cost of smaller volumes. XRM is useful for imaging thick and opaque samples. Here is a comparison of some of the aEyes used vEM techniques:

Serial block-face scanning electron microscopy (SBEM): SBEM involves the sequential removal of thin sections from a sample block while imaging the exposed surface with an electron microscope. It provides high-resolution images of large samples, making it useful for studying the fine structure of tissues, organs, and even whole organisms.

Focused ion beam scanning electron microscopy (FIB-SEM): FIB-SEM uses a focused ion beam to remove thin layers of a sample, which are then imaged with an electron microscope. Like SBEM, FIB-SEM allows for high-resolution imaging of large volumes, but it has the advantage of being able to image samples that are difficult to section, such as materials, thin films, and devices.

Transmission electron microscopy (TEM) tomography: TEM tomography involves imaging a series of thin sections of a sample with a transmission electron microscope and then reconstructing a 3D image from the collected data.

TEM tomography provides the highest resolution of all vEM techniques, but it is limited to small volumes and requires specialized sample preparation.

Serial section transmission electron microscopy (ssTEM): ssTEM involves physically cutting a sample into ultrathin sections and imaging each section with a transmission electron microscope. It provides high-resolution images of small volumes, making it useful for studying the ultrastructure of cells and tissues. However, like SBEM, ssTEM is limited by the need to physically section the sample.

X-ray microscopy (XRM): XRM uses X-rays to image samples in 3D. It provides lower resolution than electron microscopy, but it has the advantage of being able to image thick and opaque samples, such as rocks, bones, and fossils.

Multi-view Autostereoscopic Displays: Displays able to show different stereo image pairs in different viewing zones without glasses are referred to as multi-view autostereoscopic displays.

Holography uses a two-step process to produce light fields of static objects. First, the real object is illuminated by a laser in a dark room. A film, i.e., similar to the ones used for analog cameras, records the light reflected by the object. This process is depicted in FIG. 17. The atoms in the material of the film are re-organized according to the outgoing light distribution and can thus be seen as a recording of the light field. Second, to display the hologram, the same film is illuminated by a laser in the same direction as during the creation phase. The viewer sees the same outgoing light as the object sent out during the creation phase independent of the viewing angle and position. This process can be used to create photorealistic virtual objects.

aEyes Microlens Arrays (aEyes-M-Arrays) is a microlens array technology and artificial intelligence in the medical field. It involves the use of microlens arrays to enable new medical imaging and sensing techniques, which are then optimized using AI algorithms to enhance their diagnostic and therapeutic capabilities. aEYES-M-Arrays represents an exciting new direction for the field of medical imaging and sensing, with the potential to revolutionize diagnosis and treatment by enabling highly accurate and non-invasive imaging and sensing of tissues and organs.

aEyes-M-Arrays has the potential to revolutionize medical imaging by enabling high-resolution, non-invasive, and real-time imaging of tissues and organs. aEyes-M-arrays can be integrated into endoscopes or other medical devices, allowing for detailed visualization of internal structures and abnormalities. AI can be used to optimize the performance of the microlens array by analyzing the optical properties of the system and making real-time adjustments to improve the quality of the imaging. This can lead to faster and more accurate diagnoses, as well as real-time updated surgical planning and guidance. In addition to imaging, aEyes-M-Arrays can also be used for sensing applications, such as detecting and measuring biomarkers or other substances in bodily fluids. By integrating microlens arrays with biosensors, it is possible to create highly sensitive and specific diagnostic tools for diseases such as cancer, diabetes, and infectious diseases. One of the advantages of aEYES-M-Arrays is its ability to operate autonomously without the need for human intervention. This can lead to improvements in efficiency and productivity, as well as the ability to operate in remote or hazardous environments.

aEyes ML Microbial Labeling (aEyes-M-L): AI used in microbial labeling to automate and streamline the process of identifying and tagging microorganisms with molecular markers. Machine learning algorithms trained on large datasets of microbial sequence data to recognize patterns and classify sequences based on their similarity to known sequences. One example of AI microbial labeling is the use of deep learning algorithms to identify and classify microbial cells in microscopy images. By training a neural network on large datasets of annotated images, algorithms can accurately identify, and label different types of microorganisms based on their morphological features. Another example of AI microbial labeling is the use of machine learning algorithms to predict the function of microbial genes based on their sequence data. By training models on large databases of annotated genes, researchers can develop algorithms that can accurately predict the functions of unknown genes, allowing for a more detailed understanding of microbial metabolism and physiology.

Infectious diseases: Infectious diseases are caused by microorganisms belonging to the class of bacteria, viruses, fungi, or parasites. These pathogens are transmitted, directly or indirectly, and can lead to epidemics or even pandemics. The resulting infection may lead to mild-to-severe symptoms such as life-threatening fever or diarrhea. Infectious diseases may be asymptomatic in some individuals but may lead to disastrous effects in others. Despite the advances in medicine, infectious diseases are a leading cause of death worldwide, especially in low-income countries.

Autonomous AI 3D microscopy body clinical assessment can be a powerful tool for detecting and analyzing various characteristics of the body at a cellular level. Here are some potential ways that this approach could be used: In any of these applications, the use of AI-powered 3D microscopy could significantly improve the speed and accuracy of clinical assessment and diagnosis, potentially leading to earlier detection of health issues and more effective treatment options.

Cell imaging: One way to use 3D microscopy for body clinical assessment is to analyze the cellular structure and function of tissues and organs. This could involve using specialized imaging techniques, such as confocal microscopy or electron microscopy, to capture high-resolution 3D images of individual cells. Machine learning algorithms may analyze these images and identify abnormal cellular structures or functions that could indicate disease or other health issues.

Tissue analysis involves capturing 3D images of tissue samples and using machine learning algorithms to analyze the cellular structure and function of the tissue. The information gathered could help to identify potential health issues or provide insights into disease progression and treatment options.

Drug screening: Autonomous AI 3D microscopy could also be used for drug screening and development. 3D images of cells and tissues could be used to test the effectiveness of potential drugs and to identify any potential side effects or toxicity issues.

Autonomous dynamic optimization for human samples by capturing and analyzing real-time 3D images of the body in motion. In any of these applications, the use of autonomous AI 3D microscopy could provide a powerful tool for optimizing the body's movements and performance, potentially leading to improved athletic performance, reduced risk of injury, and faster rehabilitation from injury.

AI image segmentation, classification, and restoration are techniques used in Autonomous Eyes and image processing that involve the use of artificial intelligence (AI) algorithms. A brief explanation of each technique:

Image segmentation: In various arrangements, this is the process of dividing an image into multiple segments or regions based on the characteristics of the image pixels, such as color, texture, or intensity. AI image segmentation algorithms use techniques such as convolutional neural networks (CNNs) and deep learning to analyze image features and segment the image into meaningful parts.

Image classification: In various arrangements, this is the process of assigning a label or category to an image based on its content. AI image classification algorithms use techniques such as CNNs and support vector machines (SVMs) to analyze image features and classify the image into predefined categories.

Image restoration: In various arrangements, this is the process of enhancing or restoring degraded or damaged images. AI image restoration algorithms use techniques such as deep learning and generative adversarial networks (GANs) to analyze and learn from a large dataset of high-quality images, and then use that knowledge to restore degraded or damaged images.

Autonomous Eyes (aEyes) controller is, in at least one arrangement, an implementation of the screening system that uses artificial intelligence (AI) (e.g., control and recognition models) to coordinate the actions of multiple Autonomous Eyes as may be implemented as imaging devices, including various imaging components. This type of controller may be used in applications such as healthcare automation, clinical screening (bacteria, viruses, and/or cancer cells), and medical rescue operations, where Autonomous Eyes Teams work together to complete complex tasks.

The Autonomous Eyes controller operates by using data from multiple sensors and cameras installed on the aEyes to gather information about the environment and the current status of each Autonomous Eyes. It then uses this data to make decisions about the best course of action for the entire team.

The Autonomous Eyes Controller (aEyes-C) can also communicate with medical robots individually, sending commands and receiving feedback in real-time. This allows it to coordinate the actions of the aEyes to optimize performance and ensure that each Autonomous Eyes is working towards the same goal.

Some of the features of an aEyes controller for a robot team may include:

Multi-Robot Coordination: The AI cloud controller can coordinate the actions of multiple aEyes, ensuring that they work together to achieve the same objective.

Real-Time Decision Making: The controller can make decisions in real-time based on data from the sensors.

Automated Control: The controller can automate many aspects of robot control, including navigation, obstacle avoidance, and task allocation.

Learning and Adaptation: The controller can learn from actions/outcomes and adapt strategies to improve performance over time.

Autonomous Eyes Teams (aEyes-T) are a group of Autonomous Eyes that can work together to perform a task without human intervention. These teams of aEyes can use a combination of advanced sensors, machine learning algorithms, and communication technologies to coordinate their actions and achieve their goals.

aEyes DIC (Differential Interference Contrast) illumination is part of aEyes microscopy technique that enhances the contrast of transparent, unstained specimens.

aEyes DIC illumination works by splitting a polarized light beam into two beams that pass through the specimen and recombine to create interference patterns. The interference patterns are then transformed into contrast that reveals details of the specimen that would be difficult or impossible to see with conventional brightfield microscopy.

aEyes Self-Evolving Capabilities: aEyes is designed to enable constant evolution as the system continues to develop and improve technology to enable it to perform a wide range of medical tasks with high accuracy and efficiency.

Accordingly, the screening system can encompass a wide range of aspects in relation to implementing autonomous eyes within various contexts. As such, the following description and figures illustrate a medical context and generally describe a single device. However, it should be appreciated that the configuration and context of the noted device may vary to include the coordination of multiple robotic devices within various contexts.

With reference to FIG. 1, one example of a process overview 100 of the integration of an imaging device with reinforcement learning components is shown. As shown, an imaging component that is a visible light-based camera includes a multifocal lens, including lenslets 105-125. The lenslets can be optionally selected in different configurations to provide different imaging characteristics, such as a different field of view (FoV), focal points, magnification, and so on. As shown in the instant example, the FoV may vary in scale from 10 meters to 1 nanometer according to the selected arrangement of lenslets 105-125. Moreover, while five lenslets are shown, it should be appreciated that the number may vary according to the implementation, as previously described. In any case, according to the selected arrangements, as may be determined by the control model, the screening system acquires imaging data that is then provided to a recognition model for mapping and detection. The recognition model may be comprised of a single model or of a combination of different models that can be machine learning models, heuristics, or other algorithms. As shown in FIG. 1, the recognition model is represented by a series of algorithms AL-1, AL-1 to AL-n. In any case, the separate layers of, as depicted in FIG. 1, function to process the imaging data from the imaging component into a result, as described further in relation to FIG. 3.

Figure 2:
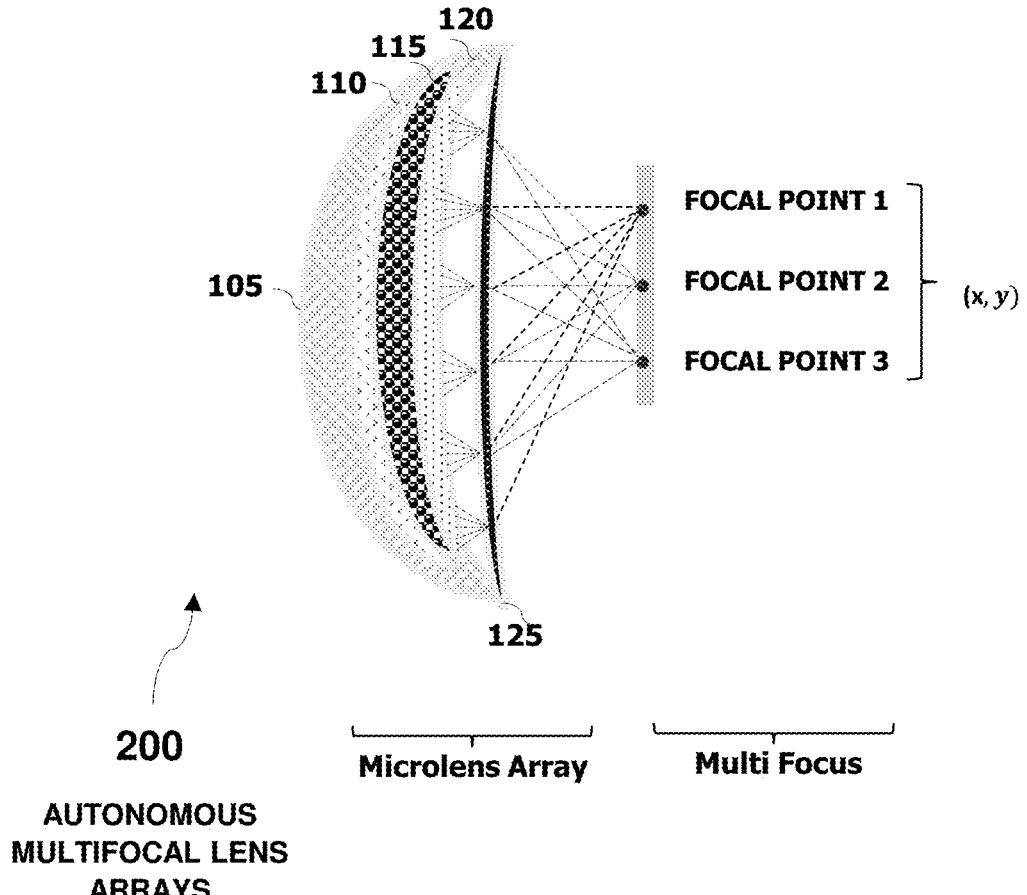
FIG. 2 is a detailed illustration of an imaging device that includes a multifocal lens.

FIG. 2 illustrates one example of the multifocal lens from FIG. 1. As illustrated, the lenslets 105-125 form a microlens array. The configuration of the mircolens array allows for a widefield of view that can provide multiple different focal points, as shown. The focal points focus on different points in the environment, such as at different locations on a patient in order to provide information about multiple different areas of a patient simultaneously. Accordingly, the multifocal lens may be associated with separate sensors or a large format sensor to dynamically acquire the focal points according to an arrangement of the lenslets. In any case, the multifocus lens is one example of an imaging component that can be integrated within an imaging device associated with the screening system. Of course, the imaging device may include multiple different imaging modalities beyond the multifocal lens.

Figure 3:
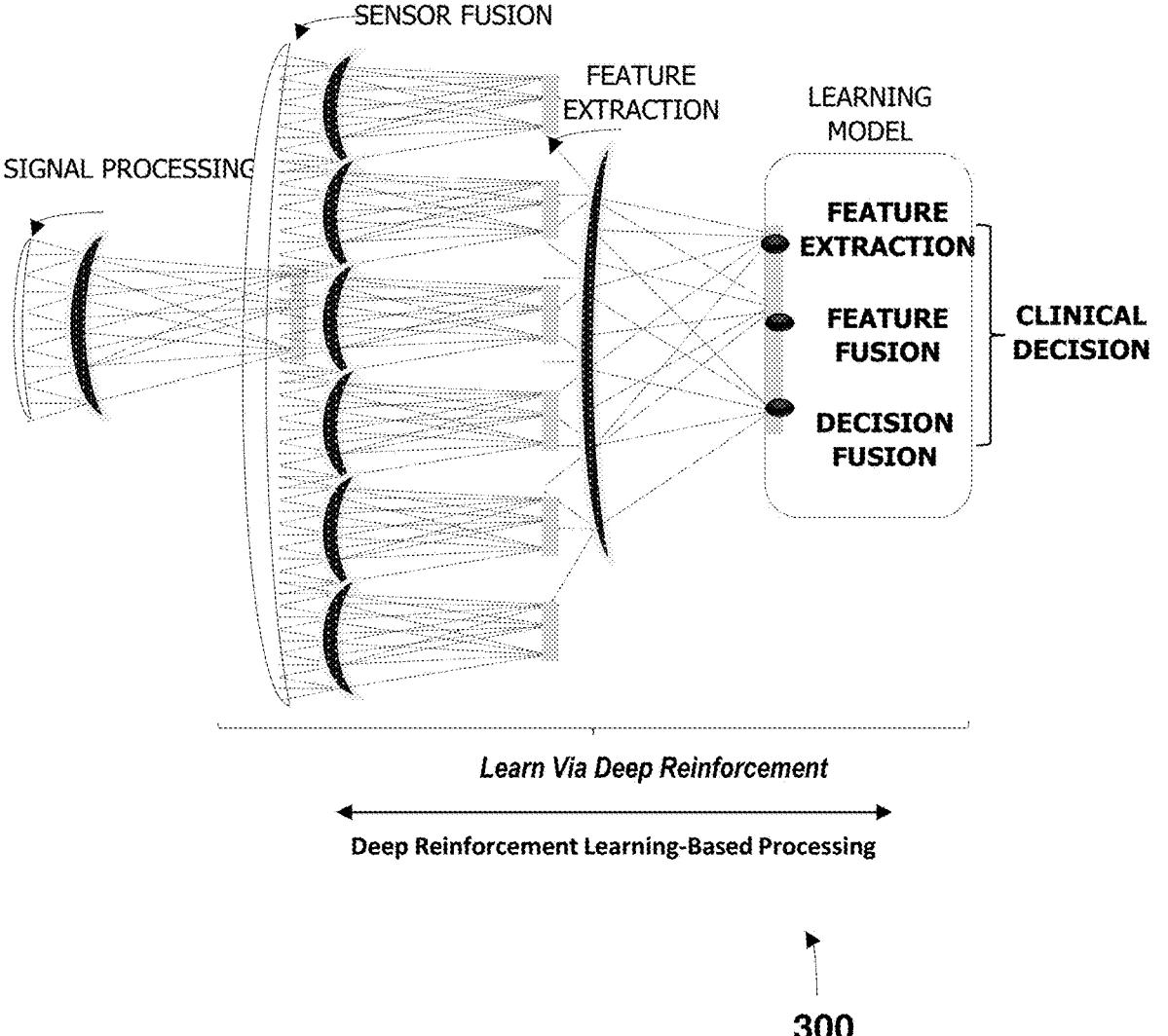
FIG. 3 is a diagram of how a neural network processes information.

FIG. 3 is a diagram 300 of how a neural network, such as the recognition model, processes information. In particular, the diagram illustrates multiple separate tiers that implement, for example, separate algorithms of the recognition model, which may include one or more tiers of a machine learning algorithm. In one arrangement, as shown, initial layers perform pre-processing of the imaging data in the form of signal processing to format, filter, and otherwise condition the imaging data for subsequent processing. Moreover, a sensor fusion layer may be included to combine multiple FoVs into a single image, derive depth (e.g., 3D from 2D), combine separate modalities, and so on. Subsequently, the diagram 300 illustrates a feature extraction layer that may be, for example, an encoder, such as a convolutional encoder of a CNN to extract and encode features within the processed and fused imaging data. The feature extraction process of an encoder generally involves analyzing the imaging data to generate a spatially condensed abstract representation of features depicted in the data. The features are, for example, representations of spatial characteristics, such as body parts, components (e.g., cell organelles), attributes, and so on. The illustrated learning model may then derive inferences from the features via learned attributes to derive a result that is provided as a clinical decision (e.g., a diagnosis, intermediate determinations, etc.). As previously noted, the recognition model and associated aspects may be coupled with reinforcement learning in order to actively and without supervision continuously learn how to identify observed conditions and provide feedback for control of the imaging device.

Figure 4:
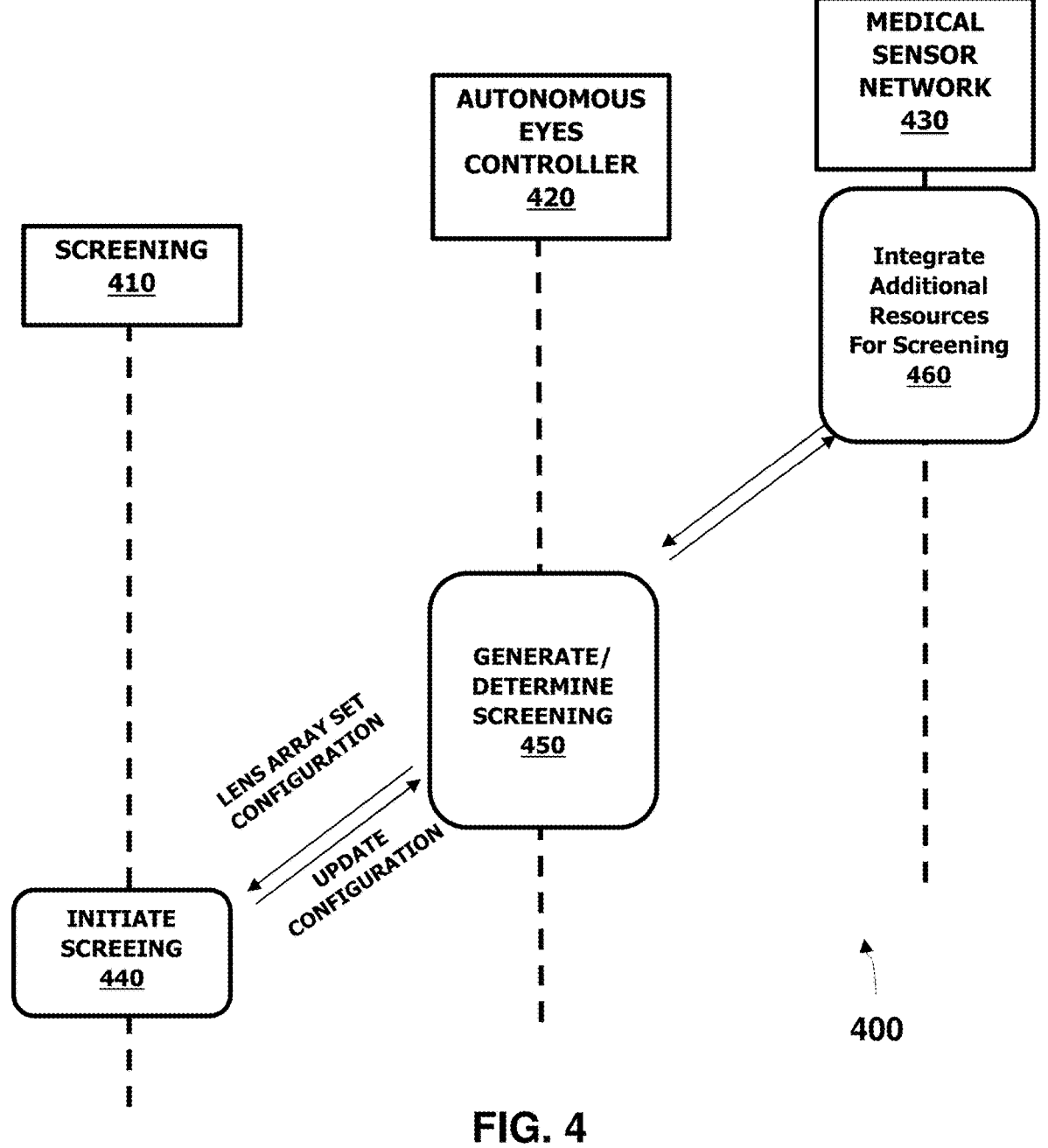
FIG. 4 is a diagram illustrating one example of how a disclosed system communicates information between components.

FIG. 4 is a diagram 400 illustrating one example of how a disclosed system communicates information between components and provides various determinations. As shown, the separate processes/entities generally include clinical screening 410, which may also include assessment, autonomous eyes controller 420, and a medical sensor network 430. The screening system described herein may encompass the screening 410 and the controller 420, while the sensor network 430 may include additional robotic devices beyond the screening system and directly associated robotic devices, such as additional automated sensors, treatment robots, procedure (i.e., biopsy) robotic devices, and so on. Accordingly, screening 410 is initiated at 440 according to available information that may include feedback from a prior acquisition of information or initial automated data, such as the detection of the presence of a patient for treatment.

In either case, the controller 420 may initially derive control settings for a lens array set that is provided as a configuration to the device. This process of configuring the imaging device occurs iteratively with each round of results informing how the configuration is updated over a subsequent iteration. The controller 420 applies the control model to the acquired information to derive the configuration of the imaging device and update the configuration until there is a determination that the clinical screening and assessment is complete, such as when a diagnosis of a condition is determined, or the patient is no longer to be monitored. In one or more aspects, the controller 420 may determine that updating the configuration for continued clinical screening and assessment involves integrating additional resources into the clinical screening and assessment, as noted at 460 via a medical sensor network. Thus, the controller may communicate over a communication network with various automated systems to request assistance for functionality that is not available in the imaging device. For example, the controller 420 may request particular procedures, such as biopsies, and additional imaging modalities (e.g., MRI, CT scans, etc.) that involve the use of additional robotic systems. As such, the controller 420 can communicate the necessary information and cause the additional systems to perform functions that facilitate the screening process. In one or more arrangements, the additional systems may perform the functions and provide the acquired information to the controller 420 for subsequent action, such as a determination of further clinical screening and assessment.

Figure 5:
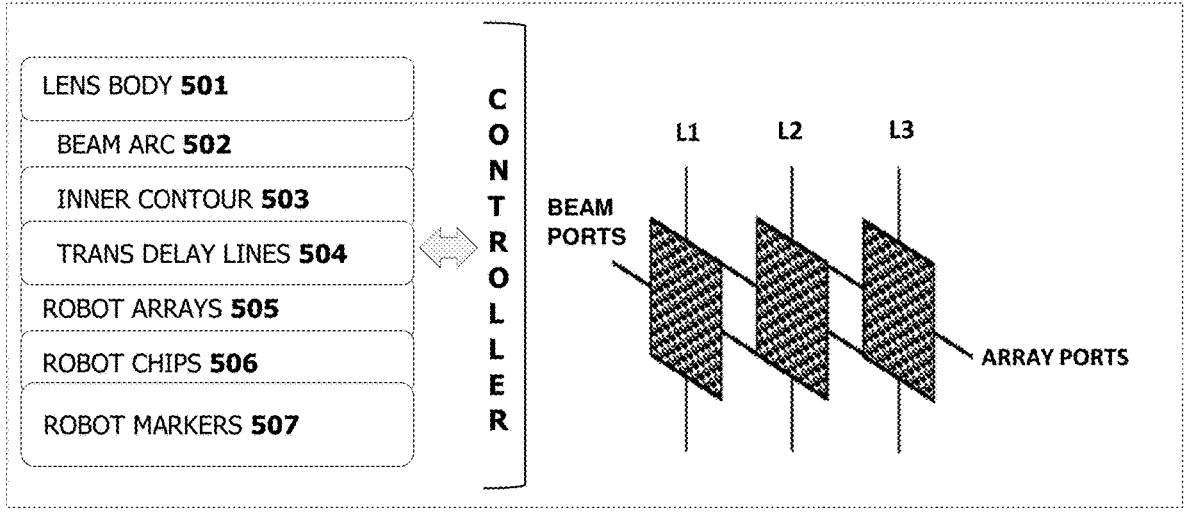
FIG. 5 illustrates one example of a controller.

FIG. 5 illustrates one example of a controller 500 and associated multi-lens array. For example, As shown, the controller 500, which may be implemented as part of the clinical screening and assessment system, includes various modules. The modules include a lens body, robot arrays, robot chips, and robot markers. The lens body itself involves a beam arc, inner contour, and trans delay lines. As shown, the multi-lens array may be configured with multiple separate arrays, shown as L1, L2, and L3 that are arranged with beam ports and array ports to facilitate transmission of light and the selective arrangement of the array by the controller. Accordingly, the multi-lens array may be controlled by the controller.

The controller can include include various modules and control various components, such as the following: Lens body 501: The lens body houses the multiple lenses in the multi-lens array. Moreover, the controller may interact with a beam arc 502, inner contour 503, and trans delay lines 504. Robot arrays 505: The robot arrays are responsible for moving the lenses in the multi-lens array to different positions. Robot chips 506: The robot chips control the robot arrays. Robot markers 507: The robot markers are used to track the positions of the lenses in the multi-lens array.

The controller, in FIG. 5, controls the multi-lens array by varying the attributes of the component to acquire the imaging data. For example, the controller can vary the following attributes: The position of the lenses in the multi-lens arrays. The focus of the lenses and the aperture of the lenses and the exposure time of the camera.

The controller can also be used to process the imaging data to generate images that are optimized for clinical screening and assessment. For example, the controller can be used to generate images that are enhanced for contrast or that have certain features highlighted.

For example, the controller and associated multi-lens array can be used in a clinical screening and assessment system in which the patient is positioned under the multi-lens array. The AI autonomous controller controls the multi-lens array to acquire a series of images of the patient. This controller processes the images to generate images that are optimized for clinical screening and assessment to identify abnormalities more quickly and accurately.

For example, the controller can combine multiple optical imaging modalities, such as fluorescence, confocal, and optical coherence tomography imaging. To enable enhanced contrast fluorescence imaging, a custom contrast agent may be implemented by attaching Cy5.5 to a quenched uPa vulnerable sequence. Analysis of the cleaved increase in fluorescence correlates with the presence of cancer in the tissue. The contrast agent and fluorescent microscopy gives an initial estimate of residual cancer on the surface of the tissue. However, because evaluation by fluorescence microscopy alone can be subject to non-specific positive margin highlighting, the utility of adding OCT and RCM becomes crucial in margin analysis. The RCM provides submicron detail to inform tissue-type classification, and guide OCT data segmentation, which provides volumetric mapping of the extent of the tumor infiltration. By using the FL mode to identify areas of highly suspicious for presence of cancer, the acquisition time can be greatly reduced during RCM/OCT imaging, which is critical for intraoperative utility. The information from the three modalities was combined in an image-processing regimen to automatically detect the cancer margins in 3D very effectively.

Figure 6:
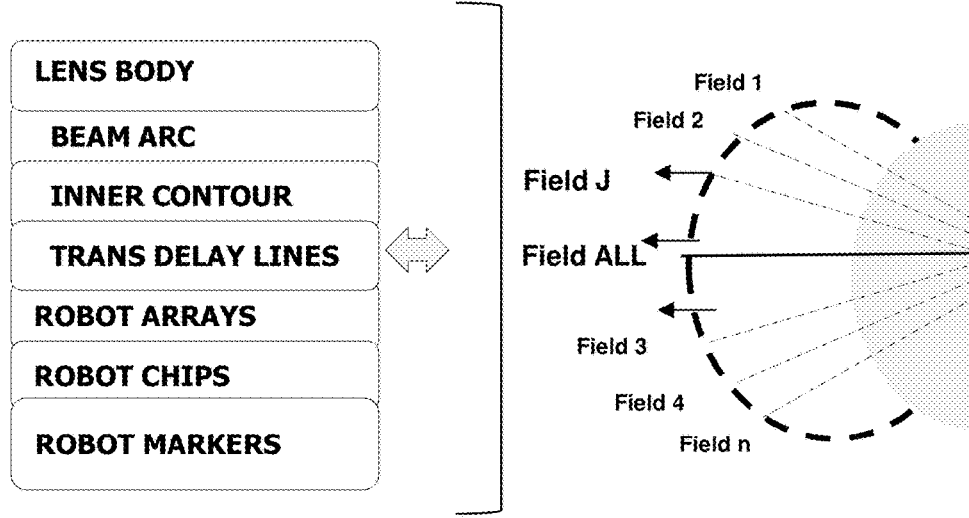
FIG. 6 illustrates an additional example of a controller.

FIG. 6 illustrates an additional example of the controller of FIG. 5. As shown, the imaging device 600 associated with the controller is arranged with an autonomous lens array that, for example, provides selectively capturing various FoVs. That is, the arrangement of lenses permits the device 600 to capture multiple separate FoVs simultaneously.

Figure 7:
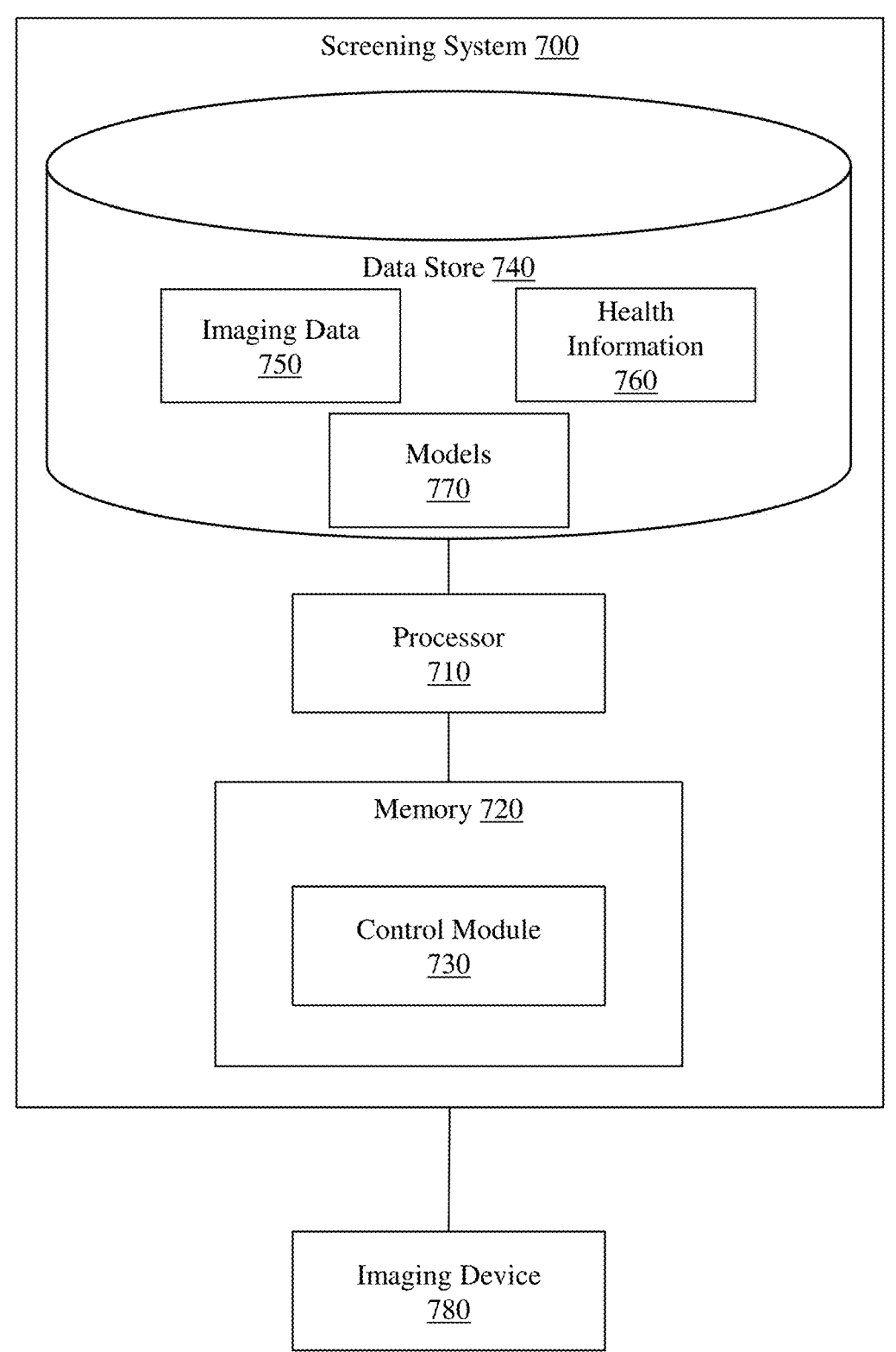
FIG. 7 illustrates one embodiment of a screening system that may be implemented with an imaging device to perform autonomous screening of a patient.

With reference to FIG. 7, one embodiment of a screening system 700 is illustrated. The screening system 700 is shown as including a processor 710. Accordingly, the processor 710 may be a part of the screening system 700, or the screening system 700 may access the processor 710 through a data bus or another communication path as a shared resource (e.g., a distributed processing environment). Thus, the processor 710 may communicate with the screening system 700 through a communication network or may be co-located with the screening system 700 (e.g., within a screening robot that is static or mobile). In further aspects, the screening system 700 may include various controllers in addition to the processor 710 that controls various subassemblies of a clinical screening and assessment robot. In one embodiment, the screening system 700 includes a memory 720 that stores a control module 730. The memory 720 is a random-access memory (RAM), read-only memory (ROM), a hard-disk drive, a flash memory, or another suitable memory (either volatile or non-volatile) for storing the control module 730 and/or other information used by the screening system 700. The control module 730 is, for example, computer-readable instructions within the physical memory 720 that, when executed by the processor 710, cause the processor 710 to perform the various functions disclosed herein. Moreover, the screening system 700 is generally embedded within the screening and assessment robot to provide various controls and decision-making processes therein. As such, the screening system 700 may be operatively connected with a communication bus within the clinical screening and assessment robot to facilitate various functions described herein.

Continuing with FIG. 7 and a general embodiment of the clinical screening and assessment system 700, in one or more arrangements, the screening system 700 includes a data store 740. The data store 740 is, in one embodiment, an electronic data structure (e.g., a database) stored in the memory 720 or another electronic memory that is configured with routines that can be executed by the processor 710 for analyzing stored data, providing stored data, organizing stored data, and so on. Thus, in one embodiment, the data store 740 stores data used by the control module 730 in executing various functions. In one embodiment, the data store 740 includes imaging 750, health information 760, models 770, and other information/functional data used by the screening system 700.

Moreover, as illustrated in FIG. 7, the screening system 700 is operably connected with an imaging device 780. While shown as separate components, the screening system 700 can be, in one or more arrangements, integrated with the imaging device 780. In either case, the screening system 700 broadly functions to control acquisition of the imaging data 750 via the imaging device 780 and/or through additional clinical screening and assessment devices with which the screening system 700 may communicate.

In general, the imaging data 750 includes observations from the imaging device 180 but may also include observations from additional sensors that are activated in support of a clinical screening and assessment/assessment process led by the screening system 700. Thus, the imaging data 750 can include observations from medical sensors and other sensors that are not specific to medical uses. Medical sensors may be sensors of the screening system 700 that provide observations of the patient, such as blood pressure monitors, heart rate monitors, temperature sensors, and so on. The sensors may also be general use sensors, such as cameras, microphones, and so on. In general, the sensors implemented by the screening system 700 and other robots are not intended to be limited but may encompass a wide range of sensors in support of the clinical screening and assessment/assessment process to provide accurate diagnoses.

To acquire the imaging data 750 about the patient, or at least a portion of the imaging data 750, the screening system 700 may include, or at least functions in cooperation with, a communication system. In one embodiment, the communication system communicates according to one or more communication standards. For example, the communication system may be wired, wireless, or a combination thereof. The communication system can include multiple different antennas/transceivers and/or other hardware elements for communicating at different frequencies and according to respective protocols, whether wired or wireless. The communication system, in one arrangement, communicates via a communication protocol, such as a WiFi, DSRC, V2I, V2V, or another suitable protocol for communicating between the screening system 700 and the respective robots. Moreover, the communication system, in one arrangement, further communicates according to a protocol, such as the global system for mobile communication (GSM), Enhanced Data Rates for GSM Evolution (EDGE), Long-Term Evolution (LTE), 5G, or another communication technology that provides for the screening system 700 communicating with various other systems and/or other robots (e.g., other clinical screening and assessment/sensor robots in a team). In any case, the screening system 700 can leverage various communication technologies to provide communications to other entities and/or receive information from other entities, such as the imaging data 750, the health information 760, and so on.

The health information 760 is, in one or more arrangements, information in addition to the imaging data 750 that the system 700 may initially or subsequently acquire about the patient that facilitates determining diagnoses. It should be noted that while the screening system 700 is shown as including the health information 760, this information is optionally provided and the clinical screening and assessment process implemented by the control module 730 generally functions without input of the health information 760 but may supplement determinations, such as an initial acquisition with such information. Moreover, the control module 730, in one or more approaches, includes various machine learning models (i.e., models 770) to process the imaging data 750 into meaningful observations and control signals. The machine learning models include, for example, detection, classification, and correlation models that analyze the imaging data 750 to determine how to control the imaging device 780 to facilitate a clinical screening and assessment process.

As outlined above, the models 770 generally include at least two models, a control model, and a recognition model. As previously noted, the separate models may be comprised of sub-models that perform separate specific subfunctions in support of the clinical screening and assessment process. In one arrangement, the recognition model functions to process the imaging data 750 into determinations about what is observed within the data, such as conditions of a patient. The recognition model may take various forms depending on the implementation and as outlined previously but can be a CNN or other model that processes spatial data to detect and identify various features depicted therein. The control model, in one or more arrangements, uses the results from the recognition model to generate a focus point for the imaging device 180 along with attributes of how to configure the imaging device 180, as will be described in greater detail subsequently.

Figure 8:
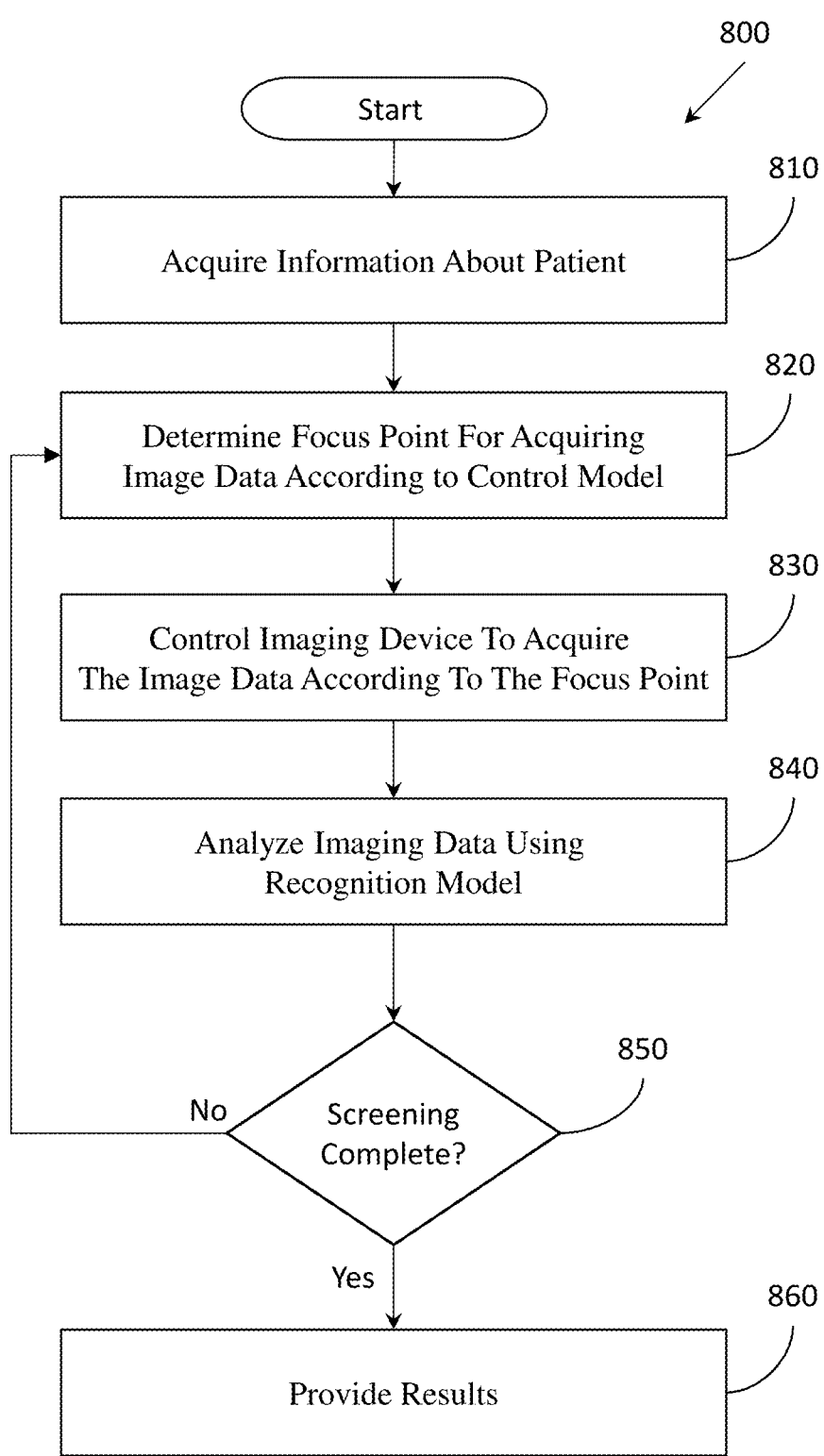
FIG. 8 is a flowchart illustrating one embodiment of a method associated with autonomous screening of a patient.

Additional aspects of autonomous clinical screening and assessment will be described in relation to FIG. 8. FIG. 8 illustrates a flowchart of a method 800 that is associated with autonomous clinical screening and assessment of a patient. Method 800 will be discussed from the perspective of the screening system 700 of FIG. 7 as implemented within a healthcare ecosystem that may include various medical sensors and autonomous systems, such as autonomous robotic systems for acquiring information and performing procedures. While method 800 is discussed in combination with the screening system 700, it should be appreciated that the method 800 is not limited to being implemented within the screening system 700 but is instead one example of a system that may implement the method 800.

At 810, the control module 730 initiates clinical screening and assessment of a patient. In various arrangements, the control module 730 may perform different functions to initiate clinical screening and assessment. For example, in one approach, the control module 730 initially acquires the health information 760 from a triage system in order to facilitate initial determinations about how to control the imaging device 180. In further arrangements, the control module 730 may acquire a low-quality pre-emptive scan of the environment to at least determine a location of the patient. In yet further approaches, the control module 730 simply detects motion or receives a generic initiation signal to initiate the method 800. Whichever approach is undertaken, once initiated, the control module proceeds to determine a focus point, as described subsequently.

At 820, the control module 730 determines, using the control model, a focus point for acquiring the imaging data about the patient. The focus point is, for example, an area, point, or specific region within an environment to which a FoV of the imaging device 780 is directed. Thus, the control module 730 analyzes available information, such as previously acquired imaging data 750, information acquired during initialization at 810, and/or other information that facilitates directing the imaging device 780 to determine the focus point. It should be appreciated that the focus point is generally intended to be a particular location on the patient that is indicative of a condition of the patient. Thus, prior acquisitions of the imaging data 750 generally provide specificity as to what the focus point should point. Of course, instances may occur where the patient exhibits signs of a condition in multiple locations, and thus the focus point reflects this through, for example, listing a series of focus points, indicating a widefield view, listing a prioritized set of focus points, and so on for acquiring the imaging data 750. Accordingly, when no specificity about salient aspects are available, the focus point may be a general focus point, such as a widefield view in order to determine how to subsequently proceed through iterating the method.

In addition to determining the focus point itself, the control model further provides attributes of the imaging device 780 for acquiring the imaging data 750. For example, the attributes indicate aspects about a configuration of the imaging device 780 or imagine devices 180. As one example, the attributes specify magnification/zoom of a multifocal lens, field of view, shutter speeds, and so on. Where the imaging device 780 is a different modality of imaging, such as an x-ray, magnetic resonance imaging (MRI), computed tomography (CT) scan, ultrasound, infrared, or other imaging modality, the attributes include device-specific attributes, such as exposure durations, frequency settings, and so on. In general, the control model determines settings to control the imaging devices 780 without human intervention.

At 830, the control module 730 controls the imaging device 780 according to the focus point and the attributes to acquire the imaging data 750. In one configuration, the control module 730 controls actuators and motors of the imaging device 780 to move the imaging device 780 into a position to image the patient according to the focus point and the attributes (e.g., focus, zoom (magnify), etc.). Thus, the control module 730 interprets the focus point and attributes and generates control signals that control the imaging device 780 to move and manipulate imaging components in order to acquire the imaging data 750. In one approach, the control module 730 generates a path for moving a robotic arm of the imaging device 180 on which the imaging component (i.e., camera, x-ray, etc.) is mounted. The path may include maneuvering various aspects of the robotic arm and/or a mobile base of the robotic arm in order to accurately position the imaging component. The control module 730 may define the path according to durations of actuators being active, rotations of motors, and so on. Moreover, the actuators and motors may include sensors and/or the imaging device 780 may include sensors for accurately sensing the motion in order to ensure appropriate movement that avoids impacting objects and the patient.

It should be noted that in instances where a listing of focus points is generated by the control model, whether weighted or not, the control module 730 controls, in one arrangement, the imaging device 780 to move through the focus points and acquire multiple separate instances of the imaging data 750 and/or time-series data. Thus, the focus points may define a path for acquiring a scan and/or individual points. Moreover, the process of determining the focus point(s), acquiring the imaging data 750, analyzing, and so on, as described at blocks 820-850 is iterative and involves refining the focus point(s) and reacquiring the imaging data 750 according to whether the result indicates that further investigation is to occur. Thus, the process may iterative over multiple separate acquisitions in order to provide comprehensive data for assessing the patient.

At 840, the control module 730 analyzing the imaging data 750 using the recognition model. As noted previously, the recognition module outputs a result about a condition of the patient. The result may take different forms depending on the condition itself and available information from the current iteration of acquiring the imaging data 750 and information contained with the imaging data 750. Thus, the result may specify broad aspects of the condition and/or aspects that should be further investigated. The form of the result may include annotations of the imaging data 750 (e.g., semantic segmentation of the imaging data 750 with additional highlighted aspects relating to the condition). In one approach, the result identifies a condition of the patient as depicted in the imaging data 750 and specifies a location of interest associated with the condition on the patient. Thus, the result may provide different granularities of information depending on many factors and generally functions to support a subsequent diagnosis and monitoring of the patient.

At 850, the control module 730 determines whether the clinical screening and assessment is complete. That is, in one approach, the control module 730 determines whether the result generated at 840 is sufficient clinical evidence and has an adequate confidence to provide support to a diagnosis or further action. In one arrangement, the control module 730 may iterate over the patient with subsequent acquisitions until no additional information is acquired. In a further aspect, the control module 730 compares a confidence value generated with the result and associated with a clinical screening and assessment threshold in order to determine whether the clinical screening and assessment is incomplete. In general, the clinical screening and assessment threshold may indicate, for example, a minimum confidence interval for relying on the result as being accurate and thus complete or not. Thus, to satisfy the screening threshold, the control module 730 compares the confidence value with the diagnosis threshold. Satisfying the screening threshold may be determined in different ways but is generally defined according to an inequality such as <=, <, and so on. The exact form of the comparison for satisfying the screening threshold may vary, but, as one example, the control module 730 may determine whether the confidence value is >= to the screening threshold (e.g., >=85% confidence).

Accordingly, at 850, the control module 730 makes a decision about how to proceed according to whether the clinical screening and assessment is complete or not. Thus, when the control module 730 determines that the clinical screening and assessment is complete, then the control module 730 proceeds to provide the result at block 860. Otherwise, the control module 730 proceeds to iterate over the process of method 800 again at 820. It should be appreciated that in some instances, the control module 730 determines that the present acquisition of imaging data by the imaging device 180 in particular is complete but may transition to procedures by other devices (e.g., medical robots that perform additional procedures, such as more invasive procedures (e.g., biopsies)). In this case, the control module 730 may transition to providing the result at block 860 but the clinical screening and assessment process may be re-initiated after intervention by the additional modality of analyzing the patient.

At 860, the control module 730 provides the result. In one arrangement, the control module 730 provides the result by, for example, communicating with additional devices to perform further clinical screening and assessment, including initiating one or more additional modalities to screen the patient. In general, the control module 730 provides the result to downstream logic that may generate a medical diagnosis and initiate various therapies to remedy the condition of the patient. This may involve communicating control signals to additional medical robots that function to autonomously perform therapies, such as surgeries, delivery of pharmaceuticals, and so on.

Moreover, as noted previously, the present approach is generally directed to reinforcement learning. Thus, providing the result can include performing reinforcement learning using the result. In one approach, the control module 730 trains the control model about how to position the imaging device 180 and configure the various attributes to acquire the imaging data 750, including how to operate the multifocal lens to acquire the imaging data 750 according to the attributes. Thus, the result specifies whether the imaging data 750 includes useful information about the patient and whether the form of the imaging data 750 accurately captures the information. As such, a reward function assesses whether the imaging data 750 is accurate and provides a reinforcement signal to the control model in order to train the model. This results in adapting how the control model determines focus points and attributes and may further define the control of the imaging device 780 such that the imaging device 780 realizes the desired focus points and attributes. In this way, the screening system 700 functions to learn how to screen patients without intervention from humans.

Figure 9:
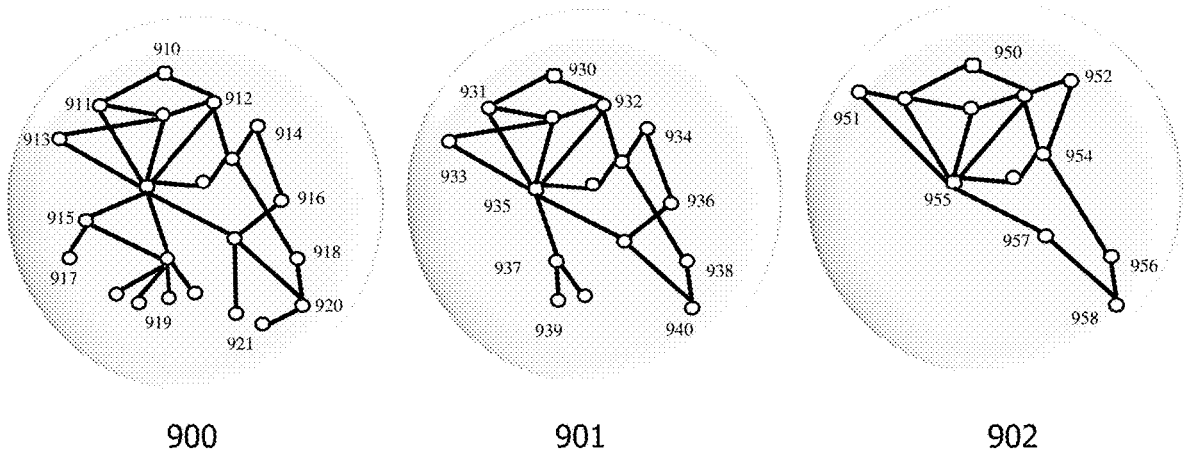
FIG. 9 illustrates example focus groups for focusing image acquisition.
Figure 9:
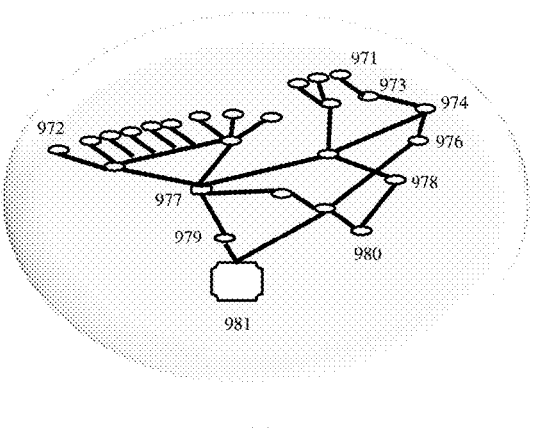

FIG. 9 illustrates examples of focus groups for how the control model may select focus points for clinical screening and assessment of a patient. For example, four separate focus groups 900-903 are shown in FIG. 9. A focus generally maps how the screening system 700 should proceed with selecting focus points according to observed aspects of a patient. Thus, in the representation of FIG. 9, the separate focus groups are shown as unstructured graphs with root nodes 910, 930 and 950. 910, 930 and 950 represent an initial entry point from which acquired information can then inform how the screening system 700 proceeds with acquiring the imaging data 750. In general, each separate focus group is associated with a different condition or class of conditions and indicates a sequence of options for acquiring the imaging data. Thus, the separate nodes are associated with a series of determinations about the patient and how to acquire further useful information based on the acquisitions and determinations. Thus, the control model may further consider the focus groups when determining how to screen the patient.

900 illustrates example focus groups for the controller to learn to identify patterns in the images and to adjust the lens array settings to optimize the image quality. 901 illustrates an example focus group reduced operator workload. 902 illustrates example focus group controller for increased accuracy. 903 illustrates examples of focus groups stitched together to create a complete 3D image and/or rapid image fusion.

900-903 illustrate examples of focus groups that are AI algorithm-based systems to control a multi-lens array and process in a way that allows the controller to learn and evolve over time. This type of controller can be used to improve the performance of a variety of imaging steps. The aEyes self-learning and evolving controller functions by, in one approach, using an algorithm set to learn from the images that it acquires. The algorithm learns to identify patterns in the images and to adjust the lens array settings to optimize the image quality. Over time, the controller becomes better at acquiring high-quality images of a variety of objects, including patients. The controller can learn from new data and adapt to new imaging conditions. Some of the benefits include the following: Improved image quality, the controller can learn to identify patterns in the images and to adjust the lens array settings to optimize the image quality, such as in 910-921. Reduced operator workload: the controller can automate the process of image acquisition and processing, which can free operators to focus on other tasks, such as with 930-940. Increased accuracy: the controller can learn to identify abnormalities in the images more accurately than human operators. Adaptability: The controller can learn from new data and adapt to new imaging conditions, such as in 950-958.

A lens array microscope is a type of microscope that uses an array of lenses to image a sample. This allows the microscope to produce images with a wide field of view and high resolution. Lens array microscopes are also very fast, making them ideal for imaging dynamic processes such as live cell imaging.

For example, controlling automatic rapid image fusion of preoperative imagery with real-time intraoperative imagery is important and can improve the accuracy and safety of surgery. This is because it allows the surgeon to see the patient's anatomy in real time, overlaid with preoperative images. This can help the surgeon to identify the tumor and other important structures, and to ensure that all the tumor is removed during surgery.

Rapid image fusion of preoperative imagery with real-time intraoperative imagery. Including image registration: this is the process of aligning the preoperative images with the real-time intraoperative images. This can be done using a variety of techniques, such as landmark-based registration, feature-based registration, and deformable registration. Image fusion: this is the process of combining the preoperative images and the real-time intraoperative images into a single image. This can be done using a variety of techniques, such as intensity-based fusion, feature-based fusion, and model-based fusion. In some cases, a combination of techniques may be used. This fusion of preoperative imagery with real-time intraoperative imagery could make surgery more accurate, safer, and less invasive. Some of the potential benefits of fusing preoperative imagery with real-time intraoperative imagery include the following elements. Improved accuracy: The fusion of preoperative imagery with real-time intraoperative imagery can help the surgeon to identify the tumor and other important structures more accurately. This can help to ensure that all the tumor is removed during surgery. Increased safety: The fusion of preoperative imagery with real-time intraoperative imagery can help the surgeon to avoid damaging important structures during surgery. Reduced invasiveness: The fusion of preoperative imagery with real-time intraoperative imagery can help the surgeon to perform less invasive surgeries. This can lead to less pain and scary for patients. Improved efficiency: The fusion of preoperative imagery with real-time intraoperative imagery can help the surgeon to perform surgery more efficiently. This can free up the surgeon's time so that they can focus on other aspects of the procedure.

971-981, multimodality image fusion is the process of combining images from multiple imaging modalities into a single image. This can be done to improve the image quality, to provide more information about the object being imaged, or to facilitate the interpretation of the images. Feature-based fusion: this technique combines the features of the images from different modalities. This can be more effective than intensity-based fusion, but it can be more computationally expensive. Model-based fusion: this technique combines the images from different modalities using a model of the object being imaged.

FIGS. 10A-B illustrate examples of an aEye live cell measuring, which can automatically measure the size, shape, and other characteristics of live cells without human intervention. The algorithms of the system 700 are trained on a large dataset of images of live cells and their corresponding measurements. This allows the algorithms to learn the features that are important for distinguishing different types of cells and for measuring their characteristics accurately. Once the algorithms are trained, they can be used to autonomously measure the characteristics of live cells in new images. This is done by first identifying the cells in the image and then segmenting the cells from the background. Once the cells are segmented, the algorithms can measure their features, such as their size, shape, and intensity.

This aEye live cell measurement has a number of advantages. First, they can save researchers a significant amount of time and effort by automating the measurement process. Second, they can be used to measure a large number of cells in a short period of time, which can be useful for large-scale studies. Third, they can be used to measure the characteristics of cells that are difficult to measure manually, such as cells that are moving or dividing. They could be used to accelerate research in a wide range of areas, such as cancer biology, developmental biology, and drug discovery.

FIG. 10A illustrates an example of focusing on single normal cell, while FIG. 10B illustrates focusing on cancer cells. Autonomously focusing on single cells by microscopy aims to automate the focusing process, allowing microscopes to focus on single cells without any manual intervention. This uses AI algorithms to train microscopes to identify and focus on single cells. This approach is used in conjunction with contrast detection or phase imaging, adaptive optics: Adaptive optics systems can be used to correct aberrations in the microscope optical path. This can improve the image quality and make it easier for the microscope to focus on single cells and 3D tracking. 3D tracking algorithms can be used to track the movement of cells in real time. This information can then be used to keep the microscope focused on the cells of interest.

Autonomous focusing can enable high-throughput screening and assessment, thereby allowing clinicians to image large numbers of cells quickly and efficiently. This is important for applications, such as drug discovery and disease diagnosis. Autonomous focus can enable live cell imaging of single cells over time. This can be used to study the dynamics of cellular processes, such as cell division, migration, and signaling. super-resolution. Autonomous focus can be used to improve the performance of super-resolution microscopy techniques. This is because super-resolution microscopy techniques utilize very precise focusing. As an example, autonomous focus can be used to track the movement of individual immune cells in real-time. This helps to understand how immune cells respond to infection and to identify new ways to boost the immune system. Autonomous focus can be used to image the development of individual stem cells, which helps to understand how stem cells differentiate into different types of cells and to identify the factors that influence this process. Using autonomous focus can also improve the performance of super-resolution microscopy techniques. This allows imaging subcellular structures that are too small to be seen with conventional microscopy.

As shown in FIG. 10A, the figure includes focus points with markers of single normal cells, while FIG. 10B includes single cancer cells distinguished by several features, including size and shape. Cancer cells are often larger and more pleomorphic 1022-1024 (irregular in shape) than normal cells 1012-1014. The nucleus of cancer cells is typically a larger and darker nucleus than normal cells. The nucleus may also be irregularly shaped or contain multiple nucleoli (the dark bodies inside the nucleus that contain ribosomal RNA). The cytoplasm of cancer cells may be less than normal cells, and the cytoplasm may be vacuolated (contain empty spaces). Cell-cell junctions 1025-1030 indicate cancer cells often have weaker cell-cell junctions than normal cells. This allows them to detach from their neighbors and invade other tissues. Mitotic figures (the structures that appear in the cell during cell division) are more common in cancer cells than in normal cells. This is because cancer cells divide more rapidly than normal cells.

Different types of cancer cells can vary in appearance under a microscope, depending on the type of cancer and the stage of the disease. However, there are some general features that are common to many types of cancer cells. It is important to note that the appearance of cancer cells under traditional microscopes can vary depending on the individual patient and the stage of the disease. This controller with wide review of tissue from different areas of the tumor to make a definitive diagnosis.

1001 and 1002 indicate that the system 700 also can automatically measure the size, shape, and other characteristics of live cells without human intervention. This is achieved by combining the controller with machine learning algorithms. The AI and ML algorithms are trained on a large dataset of images of live cells and their corresponding measurements. This allows the algorithms to learn the features that are important for distinguishing different types of cells and for measuring their characteristics accurately. Once the algorithms are trained, they can be used to autonomously measure the characteristics of live cells in new images. This is done by first identifying the cells in the image and then segmenting them from the background. Once the cells are segmented, the algorithms can measure their features, such as their size, shape, and intensity. This autonomous live cell measuring has several advantages over traditional microscopes. First, they can save a significant amount of time and effort by automating the measurement process. Second, they can be used to measure many cells in a short period of time, which can be useful for large-scale studies. Third, they can be used to measure the characteristics of cells that are difficult to measure manually, such as cells that are moving or dividing.

In one example corresponding to FIG. 10A, localization of healthy structures centers on the development of devices and software that can accurately sense structures within tissues, integrating seamlessly with surgical tools and workflows.

1021-1035 of FIG. 10B show how aEyes Contrast Agent Sets, aEyes labeling sets, aEyes marker Sets, and aEyes signature sets are all substances that can be used to make things more visible. However, they have different purposes and properties.

aEyes Contrast Agents Sets (aEyes-CAS) are used to improve the visibility of certain tissues and organs in medical imaging procedures. They are typically administered to the patient intravenously, orally, or rectally, Such as Indocyanine Green, Cytalux, or Gleolan and CD24, B7-H3 markers, annexin, fibroblasts, and/or macrophages etc.

A further example of aEyes-CAS, includes a quenched contrast agent, which is activated by cancer specific enzymes, such as urokinase plasminogen activators (uPA). In particular, this involves is a type of imaging probe that can be used to detect and image cancer tumors. uPA is an enzyme that is overexpressed in many types of cancer, including breast cancer, prostate cancer, and lung cancer. Quenched contrast agents are designed to be non-fluorescent in their original state. However, when they come into contact with uPA, they are cleaved by the enzyme, which releases the fluorescent signal. This allows the contrast agent to be visualized using imaging techniques such as fluorescence imaging and optical imaging. Quenched contrast agents have several advantages over traditional imaging probes. First, they are more specific for cancer cells, which helps to reduce background noise and improve the accuracy of imaging. Second, they are more sensitive than traditional probes, which means that they can detect smaller tumors. Third, they are less toxic than traditional probes, making them safer for patients. Several quenched contrast agents that are activated by uPA: One example is a probe called UPA-FRET, which is a fluorescently labeled peptide that is cleaved by uPA. Another example is a probe called UPA-Cy5, which is a near-infrared fluorescent dye that is conjugated to a peptide substrate for uPA. Quenched contrast agents that are activated by uPA have the potential to revolutionize cancer imaging. By providing more specific, sensitive, and safer imaging probes, these agents could help to improve the early detection and diagnosis of cancer, as well as the monitoring of cancer treatment.

aEyes Labeling Sets (aEyes-LS) are substances that are used to identify or track something. They can be used in a variety of applications and quality control. aEyes-LS can be attached to objects, cells, or molecules. For example, fluorescent labels are used to track the movement of cells in scientific research, radioactive labels are used to track the distribution of drugs in the body and isotopic labels are used to identify and characterize different types of molecules.

1031-1035 show aEyes Markers Sets (aEyes-MK) that are substances that are used to indicate the presence or location of something. They can be used in a variety of applications, such as in medicine, biology, and environmental science. aEyes-MK can be attached to cells, molecules, or other substances. For example, tumor markers are used to detect and monitor cancer, cell markers are used to identify different types of cells and genetic markers are used to identify genetic variations. Marker sets include intro markers and extro markers.

1031-1035 show aEyes Intro Markers (aEyes IM) where aEyes IM sets are measurable biological characteristics that can be used to indicate the presence or absence of a disease or condition, or to monitor the effectiveness of a treatment. IM sets can be found in a variety of biological samples, including blood, urine, tissue, and saliva.

aEyes Extro Markers (aEyes EM): aEyes EM sets for autonomous systems are physical objects or features that can be detected and interpreted by autonomous systems, such as diagnostics and robots. EM can be used to provide information about the patient's conditions, such as the location, signs, and other objects. They can also be used to communicate with the autonomous system, such as to provide instructions or to indicate the desired destination.

aEyes Signature Sets (aEyes-SS) are substance, phenomenon, and patterns of clinical features that are associated with a particular disease or condition that provides clinical evidence, such as symptoms and signs. The symptoms and signs that a patient reports or exhibits can be used to create a clinical signature. For example, the presence of a fever, headache, and stiff neck is a clinical signature of meningitis. Laboratory tests: The results of laboratory tests can also be used to create a clinical signature. For example, a high white blood cell count and elevated inflammatory markers are clinical signatures of infection. Imaging studies: The results of imaging studies, such as X-rays, CT scans, and MRI scans, can also be used to create a clinical signature. For example, the presence of a mass in the lung is a clinical signature of lung cancer.

aEyes algorithm sets are a type of AI algorithm that is designed to operate without human intervention. These algorithms can learn from data and adapt to their environment, which allows them to make decisions and perform tasks without the need for human input. For example, aEyes algorithm sets are trained to identify specific patterns and features in microscopy images. This can be used to develop algorithms that can automatically identify cancer cells in images.

aEyes algorithm sets can be used to control the operation of the multimodal microscopy imaging systems and the contrast labeling and marker sets. The multimodal microscopy imaging systems can be used to image the samples, and the contrast labeling and marker sets would be used to enhance the contrast between the cancer cells and the non-cancer cells.

The aEyes Lens Array Sets can be used to provide the robot with a wider field of view and to improve the resolution of the images. The marker sets would be used to label specific proteins or other molecules in cells and tissues. This can be used to identify specific types of cells, including cancer cells.

The aEyes can be able to be used in a variety of settings, including hospitals, research laboratories, and pharmaceutical companies. This aspect can improve accuracy and efficiency of diagnosis; development of new treatments that are targeted to specific types of disease; reduce the need for invasive biopsies; and improve the ability to monitor the progression of cancer and the response to treatment.

In one or more arrangements, the system 700 provides methods for high throughput barcoding nucleic acids and/or protein inside the cells. The in-cell single cell capture method uses an individual cell itself as a compartment and delivers a plurality of unique identifiers, e.g., barcodes into the cell and captures the nucleic acid and/or protein targets within the cell directly. It significantly simplifies single cell analysis experimental setup and eliminates the need for external compartment generation. It provides a high throughput single cell expression profiling and cellular protein quantitation method, and targeted sequencing with in-cell capture will be able to significantly increase sensitivity and specificity for low frequent mutation detection, such as, somatic mutation in very early stage of cancer and truly enables early cancer detection. A spatial expression and/or variation detection method for a tissue sample is developed with the combination of the in-cell barcoding method and positional barcode on a planar array.

Multiple imaging modalities can be used to provide a more complete picture of the tumor, which can help doctors to make more accurate diagnoses and to plan more effective treatments. Multiple imaging modalities can be used to create a 3D model of the tumor, which can help surgeons to plan the surgery more precisely. Multiple imaging modalities can be used to guide the delivery of therapy, such as radiation therapy or chemotherapy. Multimodality image fusion can improve the image quality by combining the strengths of multiple imaging modalities into a single fused output. For example, MRI can provide high-resolution images of soft tissue, while CT can provide high-contrast images of bone. By fusing these two images, it is possible to obtain a more detailed image of the anatomy. Multimodality image fusion can increase the amount of information available about the object being imaged. This is because each imaging modality provides different information about the object. For example, MRI can provide information about the structure of the tissue, while PET can provide information about the function of the tissue. By fusing these two images, it is possible to obtain a more complete understanding of the object. Multimodality image fusion can improve the interpretation of images by making it easier to identify features of interest. For example, it can be difficult to identify a tumor in a CT image. However, by fusing the CT image with an MRI image, it may be easier to identify the tumor because the MRI image can provide more information about the soft tissue.

Focusing the lenses in the array on different parts of the body and then stitching the images together can provide for creating a complete 3D image. This image could be used for a variety of purposes, such as diagnosis. The 3D image could be used to diagnose diseases and conditions that may be difficult to see using traditional imaging methods, such as X-rays and MRI scans. For example, the image could be used to identify tumors or other abnormalities in human organs. Surgery: The 3D image could be used to plan and guide surgery. For example, the image could be used to help surgeons visualize the location of a tumor before surgery or to guide a surgical instrument to a specific location in the human body. Treatment planning: The 3D image could be used to plan and monitor the effectiveness of treatment for diseases such as cancer. For example, the image could be used to track the size and location of a tumor over time to see how it is responding to treatment. For example, using this system for localization and visualization in surgery to provide real-time feedback to medical professionals during medical imaging procedures, enhancing diagnostic accuracy and treatment decision-making.

The system plays a pivotal role in evaluating a patient's risk of developing various diseases, including heart disease, cancer, and Alzheimer's disease. This information serves as the foundation for tailoring personalized prevention and treatment strategies. For instance, an AI system can identify individuals at a high risk of developing heart disease and recommend tailored lifestyle modifications or medications to mitigate that risk.

Intraoperative Detection of Anatomical Structures (AEIDAS): In surgical contexts, precise localization, and visualization of critical anatomical structures such as nerves, blood vessels, and organs are of paramount importance. These structures are often concealed beneath layers of soft tissue and can be challenging to discern under standard operating room lighting. Furthermore, the similarity in color and texture between critical structures and surrounding tissue adds complexity to identification. AEIDAS addresses these challenges by leveraging multiple imaging modalities with varying penetration depths. For instance, optical coherence tomography (OCT) is employed to image deeper tissues, while multiphoton microscopy is utilized for high-resolution imaging of superficial tissues.

Labeling contrast control: in general, in optical imaging, a lack of contrast can exist because many biological tissues exhibit optical similarity, thereby making differentiation difficult. AEIDAS surmounts this hurdle by employing diverse contrast mechanisms. For example, fluorescence microscopy enables the visualization of specific molecules or proteins, while second harmonic generation (SHG) microscopy facilitates the imaging of collagen fibers. AEIDAS integrates artificial intelligence (AI) technologies and advanced imaging methods to automatically identify and visualize critical anatomical structures during surgery. The process may include the following:

System Real-time Imaging: High-resolution imaging techniques, such as intraoperative MRI, CT scans, ultrasound, or endoscopy, capture real-time images of the surgical site.

System Data Acquisition and Preprocessing: Images are processed by an AI system specially designed to enhance their quality and prepare them for analysis.

System Data Analysis (SDA): AI algorithms, trained on extensive datasets of annotated anatomical images, process the images, identifying various anatomical structures based on patterns, shapes, and anatomical landmarks.

System Automated Structure Detection (SASD): The AI system autonomously detects and labels key anatomical structures in the images, including blood vessels, nerves, organs, and other relevant structures.

By combining AI's data processing capabilities with advanced imaging modalities, AEIDAS significantly enhances surgical precision, enabling surgeons to navigate complex anatomical landscapes with greater confidence and accuracy.

These solutions utilize existing staining agents or explore novel staining agents to be applied post-specimen removal.

Clinical example: for precise cancer localization for intraoperative microscopic imaging of resected specimens and automated image classification. This uses contrast agents, labeling cancer cells and seeing the tumor microenvironment with aEye measurements 1003 for assessment of cancer surgical margins.

Real-time Feedback (AERF): AI-generated labels and information are displayed instantly on a monitor or heads-up display, providing surgeons with live visual cues regarding the positions of critical anatomical structures.

Augmented Reality Integration (AEAR): AR technology overlays AI-generated labels onto the surgeon's view of the surgical site, enhancing navigation and precision during procedures.

Continuous Tracking (AECT): Throughout the surgery, the AI system continually tracks the positions of anatomical structures and updates its analysis to adapt to changes in the surgical field.

Alerts and Notifications (AEAN): If potential risks, such as proximity to vital structures, are detected by the AI, it generates alerts for the surgical team, enabling proactive measures to prevent inadvertent damage.

Adaptive Learning (AEAL): The system, in one approach, continuously learns from each surgical case, fine-tuning their algorithms and improving accuracy over time.

Moreover, a multimodal optical microscopy system is introduced to visualize tumor margins during surgery. The system combines confocal microscopy, OCT, and fluorescence imaging to examine the tumor and surrounding tissue. Images are then analyzed to pinpoint tumor margins. This system can also be integrated with a surgical microscope, equipped with modules for confocal microscopy, OCT, and fluorescence imaging. The fusion of images from these modalities creates a high-resolution, in-depth view of tumor margins to guide surgeons during resection. This aEye system provides real-time information about tumor margins FIG. 10B 1003, even in challenging scenarios where margins are obscured. It facilitates complete tumor removal, reduces complications, and enhances patient outcomes.

Autonomous Eye In-vivo Visualization (AEVV) for Surgical Procedures: AEVV plays a pivotal role in surgeries, particularly in oncology, ensuring thorough removal of residual tumor tissue and confirming resection completeness. This approach integrates algorithms and advanced imaging for real-time, automated assessment during procedures.

Real-time Imaging (AERI): High-resolution imaging modalities like intraoperative MRI, CT scans, ultrasound, or endoscopy capture real-time surgical cavity images.

Data Acquisition and Processing: AI processes and interprets these images, identifying various tissue types and structures within the surgical cavity.

Tumor Margin Assessment: AEVV assesses the surgical cavity for residual tumor tissue, highlighting areas needing attention or signaling potential concerns.

Real-time Feedback: The system provides live feedback through a visualization interface on a monitor or heads-up display, aiding surgeons with AI-generated overlays on the surgical site.

Augmented Reality Integration: AR technology overlays AI-generated information onto the surgeon's view, enhancing context and guidance during surgery.

The system can impact various areas as follows:

Contrast Agent Specificity: AI algorithms can enhance the specificity of contrast agents, making them more targeted and effective in highlighting specific structures or molecules within a sample. Machine learning models can analyze real-time data from the microscope, adapt the choice of contrast agents, and optimize imaging parameters to achieve the highest contrast and specificity for different applications, such as cancer detection or cell biology studies.

Image Field of View: Autonomous microscopes powered by AI can intelligently scan and capture images over larger and more complex fields of view. AI-driven navigation can automatically identify regions of interest within a sample and adjust the field of view, accordingly, reducing the need for manual adjustments.

Imaging Resolution: AI can improve imaging resolution by using techniques such as super-resolution microscopy, where AI algorithms enhance the quality of images beyond the physical limits of the microscope.

Deep learning models can denoise images and correct aberrations, leading to sharper and more detailed microscopy results.

Imaging Types: AI can enable multi-modal imaging, allowing researchers to acquire different types of data from the same sample simultaneously. For example, combining fluorescence, brightfield, and phase-contrast imaging in real-time for a more comprehensive analysis. Autonomous microscopes can switch between imaging modalities based on the specific requirements of the sample or experiment, reducing the need for manual adjustments.

Imaging Time: AI can significantly reduce imaging time by optimizing the data acquisition process. For example, AI algorithms can predict the best locations to capture images, reducing the number of unnecessary scans. Real-time analysis of acquired data can trigger immediate adjustments to imaging parameters to capture critical information efficiently.

Specificity: AI algorithms can enhance the specificity of microscopy techniques by precisely targeting the structures or molecules of interest within a sample. This specificity is crucial in applications like disease diagnosis and drug discovery. Autonomous microscopes can adapt their imaging techniques in real-time based on the specific requirements of the sample, ensuring that the relevant features are highlighted with high specificity.

Sensitivity: AI can improve the sensitivity of microscopy by enhancing the detection of faint signals or low-abundance molecules. Machine learning models can distinguish subtle differences in contrast or intensity, making it possible to detect and quantify minute changes in samples, such as early-stage disease markers.

Usability: Future AI-powered autonomous microscopes will prioritize usability, making them more accessible to researchers and clinicians with varying levels of expertise. User-friendly interfaces and intuitive controls, guided by AI, can simplify the operation of microscopes and data analysis, reducing the learning curve.

Manufacturing Standards: The development of AI-powered autonomous microscopes will likely involve the establishment of manufacturing standards to ensure consistent quality and performance. Industry standards can help ensure that these advanced microscopy systems meet safety, accuracy, and reliability criteria, making them suitable for research, clinical, and industrial applications.

The described screening system and associated robotic device are, in one or more arrangements, part of an Autonomous Clinical screening and assessment and assessment and Recognition System (AMSRS), which can be implemented for various application areas, such as running a clinical screening and assessment line, health-related (e.g., determining the root cause of a patient's heart failure), and so on.

Detailed embodiments are disclosed herein. However, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in FIGS. 1-10, but the embodiments are not limited to the illustrated structure or application.

The flowcharts and block diagrams in the figures illustrate the architecture, functionality, and operation of possible implementations of systems, methods, and computer program products according to various embodiments. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

The systems, having means to display information, are, in various approaches, used to communicate with other individuals imaging systems. The side rear view mirror assembly includes a base to connect it to the robot, a mirror case fixed to the base, at least one light source to display forward through a lens an emoticon or other symbol, and at least one controller to turn the assembly on. The assembly may also include a voice recording or other sound to communicate with other individuals outside of the robot. The controller, which may be located remotely, could be pushed once or twice to turn on the light source. The light source could be used as a marker light. Alternatively, the controller could be an electrical interrupter controller which would cause the light source to flash so that the light source could be used as a turn signal or hazard lamp. Alternatively, the controller could be voice controlled. Alternatively, the controller could be gesture controlled. The side rear view mirror assembly may include a matrix of light emitting diodes, which could be color light emitting diodes, to display forward an emoticon or other symbol, a controller, and at least one controller to turn the assembly on and select what emoticon is shown. This assembly may also include a voice recording or other sound to communicate with other individuals outside of the robot, or as a turn signal, a hazard light, or a marker light. The controller, which is located remotely, could be pushed once or twice to turn on the light emitting diode array. Alternatively, the controller could be voice controlled. Alternatively, the controller could be gesture controlled.

The systems, components and/or processes described above can be realized in hardware or a combination of hardware and software and can be realized in a centralized fashion in one processing system or in a distributed fashion where different elements are spread across several interconnected processing systems. Any kind of processing system or another apparatus adapted for carrying out the methods described herein is suited. A typical combination of hardware and software can be a processing system with computer-usable program code that, when being loaded and executed, controls the processing system such that it carries out the methods described herein. The systems, components and/or processes also can be embedded in a computer-readable storage, such as a computer program product or other data programs storage device, readable by a machine, tangibly embodying a program of instructions executable by the machine to perform methods and processes described herein. These elements also can be embedded in an application product that comprises all the features enabling the implementation of the methods described herein and, when loaded in a processing system, is able to carry out these methods.

Furthermore, arrangements described herein may take the form of a computer program product embodied in one or more computer-readable media having computer-readable program code embodied, e.g., stored, thereon. Any combination of one or more computer-readable media may be utilized. The computer-readable medium may be a computer-readable signal medium or a computer-readable storage medium. The phrase "computer-readable storage medium" means a non-transitory storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: a portable computer diskette, a hard disk drive (HDD), a solid-state drive (SSD), a read-only memory (ROM), an erasable programmable read-only memory (EPROM or Flash memory), a portable compact disc read-only memory (CD-ROM), a digital versatile disc (DVD), an optical storage device, a magnetic storage device, or any suitable combination of the foregoing. In the context of this document, a computer-readable storage medium may be any tangible medium that can contain or store a program for use by or in connection with an instruction execution system, apparatus, or device.

Generally, modules, as used herein, include routines, programs, objects, components, data structures, and so on that perform particular tasks or implement particular data types. In further aspects, a memory generally stores the noted modules. The memory associated with a module may be a buffer or cache embedded within a processor, a RAM, a ROM, a flash memory, or another suitable electronic storage medium. In still further aspects, a module as envisioned by the present disclosure is implemented as an application-specific integrated circuit (ASIC), a hardware component of a system on a chip (SoC), as a programmable logic array (PLA), or as another suitable hardware component that is embedded with a defined configuration set (e.g., instructions) for performing the disclosed functions.

Program code embodied on a computer-readable medium may be transmitted using any appropriate medium, including but not limited to wireless, wireline, optical fiber, cable, RF, etc., or any suitable combination of the foregoing. Computer program code for carrying out operations for aspects of the present arrangements may be written in any combination of one or more programming languages, including an object-oriented programming language such as Java™, Smalltalk, C++, Python, or the like and conventional procedural programming languages, such as the "C" programming language or similar programming languages. The program code may execute entirely on the user's computer, partly on the user's computer, as a standalone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The phrase "at least one of . . . and . . . " as used herein refers to and encompasses any and all possible combinations of one or more of the associated listed items. As an example, the phrase "at least one of A, B, and C" includes A only, B only, C only, or any combination thereof (e.g., AB, AC, BC or ABC).

Aspects herein can be embodied in other forms without departing from the spirit or essential attributes thereof. Accordingly, reference should be made to the following claims, rather than to the foregoing specification, as indicating the scope hereof.

What is claimed is:

1. A screening system for autonomous clinical screening and assessment of a patient, comprising:

one or more processors; and a memory communicably coupled to the one or more processors and storing instructions that, when executed by the one or more processors, cause the one or more processors to:

determine, using a control model comprising a deep reinforcement learning (DRL) model, a focus point for acquiring imaging data about the patient by analyzing a condition of the patient from a prior acquisition of the imaging data to identify a location on the patient for the focus point and attributes of an imaging device;

control the imaging device according to the focus point associated with the condition to acquire the imaging data by controlling one or more actuators and motors to move the imaging device into a position to image the patient according to the focus point and to focus and zoom the imaging device to acquire the imaging data;

analyze the imaging data using a recognition model that outputs a result about the condition of the patient, the recognition model comprising a machine learning model selected from a group consisting of a convolutional neural network (CNN), a recurrent neural network (RNN), a support vector machine (SVM), and a random forest; and provide the result.

2. The screening system of claim 1, wherein the instructions to determine the focus point and control the imaging device include instructions to iteratively refine the focus point and reacquire the imaging data according to whether the result indicates that further investigation is to occur based on an assessment of the condition of the patient, including regenerating the result at separate iterations to refine a determination of the condition.

3. The screening system of claim 1, wherein the attributes of the imaging device, including a configuration of a multifocal lens for magnifying the imaging data, the multifocal lens comprising a microlens array that permits the multifocal lens to focus on multiple different focal points.

4. The screening system of claim 1, wherein the instructions to control the imaging device to focus and zoom include instructions to select a combination of individual lenses from a multifocal lens of the imaging device.

5. The screening system of claim 1, wherein the instructions to analyze the imaging data using the recognition model include instructions to identify the condition of the patient as depicted in the imaging data and specify a location of interest associated with the condition of the patient.

6. The screening system of claim 1, wherein the instructions to provide the result include instructions to perform reinforcement learning using the result to train the control model about how to position the imaging device to acquire the imaging data and to operate a multifocal lens to acquire the imaging data at a desired magnification.

7. The screening system of claim 1, wherein the instructions to provide the result include instructions to use the result with a reward function to generate a reinforcement signal with the control model.

8. The screening system of claim 1, wherein the instructions to provide the result include instructions to communicate with additional devices to perform further clinical screening and assessment, including initiating one or more additional modalities to screen the patient.

9. A non-transitory computer-readable medium for autonomous clinical screening and assessment of a patient and storing instructions that, when executed by one or more processors, cause the one or more processors to:

determine, using a control model comprising a deep reinforcement learning (DRL) model, a focus point for acquiring imaging data about the patient by analyzing a condition of the patient from a prior acquisition of the imaging data to identify a location on the patient for the focus point and attributes of an imaging device;

control the imaging device according to the focus point associated with the condition to acquire the imaging data by controlling one or more actuators and motors to move the imaging device into a position to image the patient according to the focus point and to focus and zoom the imaging device to acquire the imaging data;

analyze the imaging data using a recognition model that outputs a result about the condition of the patient, the recognition model comprising a machine learning model selected from a group consisting of a convolutional neural network (CNN), a recurrent neural network (RNN), a support vector machine (SVM), and a random forest; and provide the result.

10. The non-transitory computer-readable medium of claim 9, wherein the instructions to determine the focus point and control the imaging device include instructions to iteratively refine the focus point and reacquire the imaging data according to whether the result indicates that further investigation is to occur based on an assessment of the condition of the patient.

11. The non-transitory computer-readable medium of claim 9, wherein the instructions to determine the focus point including a configuration of a multifocal lens for magnifying the imaging data.

12. The non-transitory computer-readable medium of claim 9, wherein the instructions to control the imaging device include instructions to control one or more of: actuators and motors to move the imaging device into a position to image the patient according to the focus point and to focus and zoom the imaging device to acquire the imaging data, and wherein the instructions to control the imaging device to focus and zoom include instructions to select a combination of individual lenses from a multifocal lens of the imaging device.

13. The non-transitory computer-readable medium of claim 9, wherein the instructions to analyze the imaging data using the recognition model include instructions to identify a condition of the patient as depicted in the imaging data and specify a location of interest associated with the condition on the patient.

14. A method for autonomous clinical screening and assessment of a patient, comprising:

determining, using a control model comprising a deep reinforcement learning (DRL) model, a focus point for acquiring imaging data about the patient by analyzing a condition of the patient from a prior acquisition of the imaging data to identify a location on the patient for the focus point and attributes of an imaging device;

controlling the imaging device according to the focus point associated with the condition to acquire the imaging data by controlling one or more actuators and motors to move the imaging device into a position to image the patient according to the focus point and to focus and zoom the imaging device to acquire the imaging data;

analyzing the imaging data using a recognition model that outputs a result about the condition of the patient, the recognition model comprising a machine learning model selected from a group consisting of a convolutional neural network (CNN), a recurrent neural network (RNN), a support vector machine (SVM), and a random forest; and providing the result.

15. The method of claim 14, wherein determining the focus point and controlling the imaging device includes iteratively refining the focus point and reacquiring the imaging data according to whether the result indicates that further investigation is to occur based on an assessment of the condition of the patient.

16. The method of claim 14, wherein the attributes of the imaging device, including a configuration of a multifocal lens for magnifying the imaging data.

17. The method of claim 14, wherein controlling the imaging device to focus and zoom includes selecting a combination of individual lenses from a multifocal lens of the imaging device.

18. The method of claim 14, wherein analyzing the imaging data using the recognition model includes identifying the condition of the patient as depicted in the imaging data and specifying a location of interest associated with the condition of the patient.

19. The method of claim 14, wherein providing the result includes performing reinforcement learning using the result to train the control model about how to position the imaging device to acquire the imaging data and to operate a multifocal lens to acquire the imaging data a desired magnification, and wherein providing the result includes using the result with a reward function to generate a reinforcement signal with the control model.

20. The method of claim 14, wherein providing the result includes communicating with additional devices to perform further clinical screening and assessment, including initiating one or more additional modalities to screen the patient.

* * * * *